US011123021B2

(12) United States Patent
Shikii et al.

(10) Patent No.: US 11,123,021 B2
(45) Date of Patent: Sep. 21, 2021

(54) METHOD FOR ESTIMATING PHYSICAL CONDITION, PHYSICAL CONDITION ESTIMATION APPARATUS, AND NON-TRANSITORY COMPUTER-READABLE RECORDING MEDIUM

(71) Applicant: Panasonic Intellectual Property Corporation of America, Torrance, CA (US)

(72) Inventors: Shinichi Shikii, Nara (JP); Koichi Kusukame, Nara (JP); Aki Yoneda, Hyogo (JP); Nawatt Silawan, Osaka (JP); Shinji Uchida, Osaka (JP); Tatsuo Itoh, Osaka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 353 days.

(21) Appl. No.: 15/350,161

(22) Filed: Nov. 14, 2016

(65) Prior Publication Data

US 2017/0150930 A1 Jun. 1, 2017

Related U.S. Application Data

(60) Provisional application No. 62/261,457, filed on Dec. 1, 2015.

(30) Foreign Application Priority Data

May 20, 2016 (JP) .............................. JP2016-101969

(51) Int. Cl.
*A61B 5/00* (2006.01)
*A61B 5/026* (2006.01)
(Continued)

(52) U.S. Cl.
CPC ............ *A61B 5/7278* (2013.01); *A61B 5/026* (2013.01); *A61B 5/0261* (2013.01); *A61B 5/165* (2013.01);
(Continued)

(58) Field of Classification Search
CPC ..... A61B 5/7278; A61B 5/0261; A61B 5/026; A61B 5/165; A61B 5/20; A61B 5/0077;
(Continued)

(56) References Cited

U.S. PATENT DOCUMENTS

| 5,309,916 A | * | 5/1994 | Hatschek | ............... A61B 5/021 600/452 |
| 2005/0278093 A1 | * | 12/2005 | Kameyama | ......... B60R 16/0373 701/36 |
| 2014/0313309 A1 | | 10/2014 | Matsuo | |

FOREIGN PATENT DOCUMENTS

| JP | 2002-272708 | 9/2002 |
| JP | 2007-050144 A | 3/2007 |

(Continued)

OTHER PUBLICATIONS

The Extended European Search Report dated Apr. 5, 2017 for the related European Patent Application No. 16198407.5.
(Continued)

*Primary Examiner* — Hien N Nguyen
(74) *Attorney, Agent, or Firm* — Greenblum & Bernstein, P.L.C.

(57) ABSTRACT

A method for estimating a physical condition used by a computer includes simultaneously measuring blood flow volumes of at least two body parts of a person and estimating the person's physical condition on the basis of the blood flow volumes of the at least two body parts measured in the simultaneously measuring.

10 Claims, 14 Drawing Sheets

(51) Int. Cl.
*A61B 5/16* (2006.01)
*A61B 5/20* (2006.01)
*A61B 5/18* (2006.01)
*A61B 5/145* (2006.01)
*A61B 5/01* (2006.01)
*A61B 5/08* (2006.01)

(52) U.S. Cl.
CPC ............... *A61B 5/0077* (2013.01); *A61B 5/01* (2013.01); *A61B 5/082* (2013.01); *A61B 5/14532* (2013.01); *A61B 5/18* (2013.01); *A61B 5/20* (2013.01); *A61B 5/4094* (2013.01); *A61B 5/443* (2013.01); *A61B 5/4806* (2013.01); *A61B 5/4845* (2013.01)

(58) Field of Classification Search
CPC ......... A61B 5/18; A61B 5/14532; A61B 5/01; A61B 5/443; A61B 5/4806; A61B 5/4845; A61B 5/4094; A61B 5/082
See application file for complete search history.

(56) References Cited

FOREIGN PATENT DOCUMENTS

| | | |
|---|---|---|
| JP | 2008-186263 A | 8/2008 |
| JP | 2008-284165 A | 11/2008 |
| JP | 2009-153609 A | 7/2009 |
| JP | 2011-167398 A | 9/2011 |
| JP | 2013-085895 A | 5/2013 |
| JP | 2013-085896 A | 5/2013 |
| KR | 10-2013-0010207 A | 1/2013 |
| WO | 2014/054293 A1 | 4/2014 |

OTHER PUBLICATIONS

John Allen et al: "Microvascular imaging: techniques and opportunities for clinical physiological measurements", Physiological Measurement, Institute of Physics Publishing, Bristol, GB, vol. 35, No. 7, Jun. 9, 2014 (Jun. 9, 2014), XP020267006.

Yuhei Ikeda, et al., "Estimate Emotion Method to Use Facial Expressions and Biological Information", Proceedings of Multimedia, Distributed, Cooperative, and Mobile Symposium 2016 (DICOMO 2016), Japan, published on Jul. 6, 2016, 2016, p. 149-161, together with a partial English translation thereof.

Hiroyasu Sakamoto, et al., "A Method for Measuring Comfortableness/Uncomfortableness of Human by Analyzing Facial Images", IPSJ SIG Notes, CVIM, Japan, published on Sep. 6, 2006, 2006, 93, p. 135-142, together with a partial English translation thereof.

Communication pursuant to Article 94(3) EPC dated Sep. 28, 2020 for the related European Patent Application No. 16198407.5.

Tsiamyrtzis P et al: "Imaging Facial Physiology for the Detection of Deceit", International Journal of Computer Vision, Kluwer Academic Publishers, BO, vol. 71, No. 2, Jun. 1, 2006 (Jun. 1, 2006), pp. 197-214, XP019410113.

* cited by examiner

METHOD FOR ESTIMATING PHYSICAL CONDITION, PHYSICAL CONDITION ESTIMATION APPARATUS, AND NON-TRANSITORY COMPUTER-READABLE RECORDING MEDIUM

BACKGROUND

1. Technical Field

The present disclosure relates to a method for estimating a physical condition, a physical condition estimation apparatus, and a non-transitory computer-readable recording medium storing a program.

2. Description of the Related Art

In Japanese Unexamined Patent Application Publication No. 2002-272708, a technique for determining a person's physical condition, such as stress, fatigue, sleepiness, or an arousal level, on the basis of a pulse wave signal obtained by measuring a pulse wave caused by blood circulation is disclosed.

SUMMARY

In one general aspect, the techniques disclosed here feature a method for estimating a physical condition used by a computer. The method includes simultaneously measuring blood flow volumes of at least two body parts of a person and estimating a person's physical condition on the basis of the blood flow volumes of the at least two body parts measured in the simultaneously measuring.

With the method for estimating a physical condition in the present disclosure, a person's physical condition can be estimated without preliminary calibration.

It should be noted that general or specific embodiments may be implemented as a system, a method, an integrated circuit, a computer program, a computer-readable recording medium such as a compact disc read-only memory (CD-ROM), or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
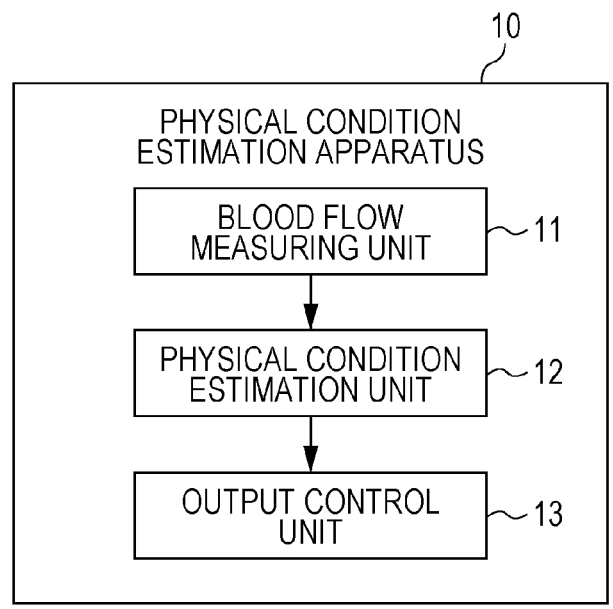
FIG. 1 is a block diagram illustrating the configuration of a physical condition estimation apparatus according to a first embodiment.

Underlying Knowledge Forming Basis of the Present Disclosure

Pulse pressure varies between individuals. In the technique disclosed in Japanese Unexamined Patent Application Publication No. 2002-2727708, therefore, calibration (adjustment) in which the pulse pressure of a subject is set needs to be performed beforehand, that is, before the subject's physical condition is determined.

One non-limiting and exemplary embodiment provides a method for estimating a physical condition without preliminary calibration and the like.

A method for estimating a physical condition according to an aspect of the present disclosure is a method for estimating a physical condition used by a computer. The method includes simultaneously measuring blood flow volumes of at least two body parts of a person and estimating a person's physical condition on the basis of the blood flow volumes of the at least two body parts measured in the simultaneously measuring.

According to the above aspect, the person's physical condition can be estimated without preliminary calibration even if the computer estimates the person's physical condition by measuring blood flow volumes that vary between individuals.

In addition, for example, in the simultaneously measuring, blood flow volumes of a first body part, whose blood flow volume hardly varies depending on the person's physical condition, and a second body part, whose blood flow volume varies depending on the person's physical condition, may be measured as the blood flow volumes of the at least two body parts.

Here, for example, the first body part may be the person's forehead. The second body part may be at least one of the person's nose, the person's lips, one of the person's hands or feet, the person's neck, and portions under the person's eyes.

In addition, for example, in the simultaneously measuring, a blood flow volume of the person's forehead and a blood flow volume of portions under the person's eyes may be measured as the blood flow volumes of the at least two body parts. In the estimating the person's physical condition, hours of sleep of the person may be estimated as the person's physical condition.

In addition, for example, in the simultaneously measuring, a blood flow volume of the person's forehead and a blood flow volume of at least one of the person's nose, the person's lips, and one of the person's hands or feet may be measured as the blood flow volumes of the at least two body parts. In the estimating the person's physical condition, a sense of warmth and coldness of the person may be estimated as the person's physical condition.

In addition, for example, in the simultaneously measuring, a blood flow volume of the person's forehead and a blood flow volume of the person's neck may be measured as the blood flow volumes of the at least two body parts. In the estimating the person's physical condition, whether the person's shoulders are stiff may be estimated as the person's physical condition.

Furthermore, for example, the method may further include estimating the person's emotion on the basis of a physiological value of the person and correcting the person's physical condition estimated in the estimating the person's physical condition on the basis of the person's emotion estimated in the estimating the person's emotion.

Here, for example, the physiological value of the person may be one of the blood flow volumes of the at least two body parts.

In addition, for example, the physiological value of the person may be a blood flow volume of a body part different from the at least two body parts.

In addition, for example, the physiological value of the person may be at least one of complexion, a heartrate, variation in the heartrate, a ratio of a low-frequency component to a high frequency component of the variation in the heartrate, R-R intervals, a pulse wave, variation in the pulse wave, a brain wave, a respiratory rate, respiratory volume, blood flow, variation in the blood flow, blood pressure, variation in the blood pressure, oxygen saturation, movement of a body part, movement of a body muscle, movement of a facial muscle, body temperature, skin temperature, skin conductance, skin resistance, the amount of sweat, and a sweating rate.

In addition, for example, in the simultaneously measuring, the blood flow volumes of the at least two body parts may be measured in a noncontact manner by radiating light having a certain wavelength onto the at least two body parts and receiving light having wavelengths different from each other.

Here, for example, in the simultaneously measuring, the blood flow volumes of the at least two body parts may be measured using a camera. For example, at least one of the simultaneously measuring and the estimating may be performed by a processor.

In addition, a physical condition estimation apparatus includes a blood flow measurer that simultaneously measures blood flow volumes of at least two body parts of a person and a physical condition estimator that estimates the person's physical condition on the basis of the blood flow volumes of the at least two body parts measured by the blood flow measurer. For example, at least one of the blood flow measurer and the physical condition estimator may include a processor.

It should be noted that these general or specific aspects may be implemented as a system, a method, an integrated circuit, a computer program, a computer-readable recording medium such as a CD-ROM, or any selective combination thereof.

The method for estimating a physical condition according to the aspect of the present disclosure and the like will be specifically described hereinafter with reference to the drawings. Embodiments that will be described hereinafter are specific examples of the present disclosure. Values, shapes, materials, components, arrangement positions of the components, and the like described in the following embodiments are examples, and do not limit the present disclosure. Among the components described in the following embodiments, ones not described in the independent claims, which define broadest concepts, will be described as arbitrary components.

First Embodiment

Configuration of Physical Condition Estimation Apparatus

FIG. 1 is a block diagram illustrating the configuration of a physical condition estimation apparatus 10 according to a first embodiment.

As illustrated in FIG. 1, the physical condition estimation apparatus 10 includes a blood flow measuring unit 11, a physical condition estimation unit 12, and a output control unit 13. The physical condition estimation apparatus 10 is implemented as a computer or the like.

Blood Flow Measuring Unit 11

Figure 2:
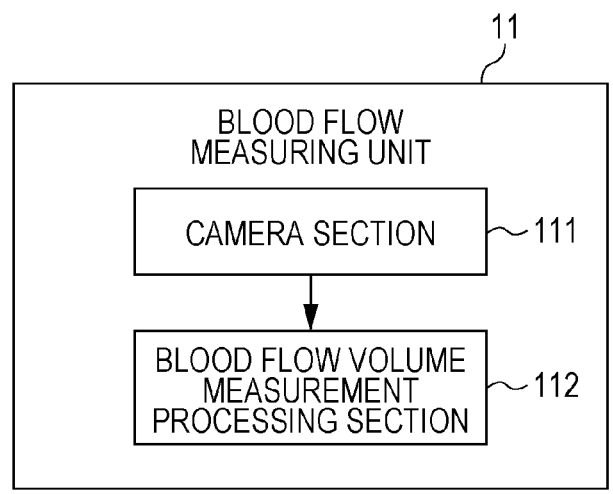
FIG. 2 is a block diagram illustrating an example of a detailed configuration of a blood flow measuring unit illustrated in FIG. 1.

FIG. 2 is a block diagram illustrating an example of a detailed configuration of the blood flow measuring unit 11 illustrated in FIG. 1.

As illustrated in FIG. 2, the blood flow measuring unit 11 includes a camera section 111 and a blood flow volume measurement processing section 112 and simultaneously measures blood flow volumes of at least two body parts of a person. The at least two body parts are a first body part, whose blood flow volume hardly varies depending on the person's physical condition, and a second body part, whose blood flow volume varies depending on the person's physical condition. For example, the first body part is the person's forehead, and the second body part is the portions under the person's eyes, the person's nose or the person's lips, one of the person's hands or feet, or the person's neck.

More specifically, the camera section 111 is a laser speckle camera, a laser Doppler blood-flowmeter, or the like. The camera section 111 radiates light having a certain wavelength onto the at least two body parts and receives light having wavelengths different from each other. The blood flow volume measurement processing section 112 measures the blood flow volumes of the at least two body parts in a noncontact manner on the basis of the light received by the camera section 111 having wavelengths different from each other.

The camera section 111 may be a camera or may be a device different from a camera, such as a milliwave sensor or a pulse oximeter, insofar as the camera section 111 is capable of simultaneously measuring the blood flow volumes of the at least two body parts.

Physical Condition Estimation Unit 12

Figure 3:
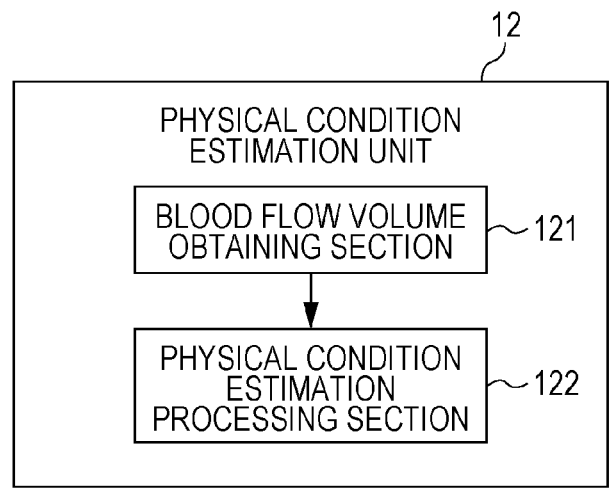
FIG. 3 is a block diagram illustrating an example of a detailed configuration of a physical condition estimation unit illustrated in FIG. 1.
Figure 4:
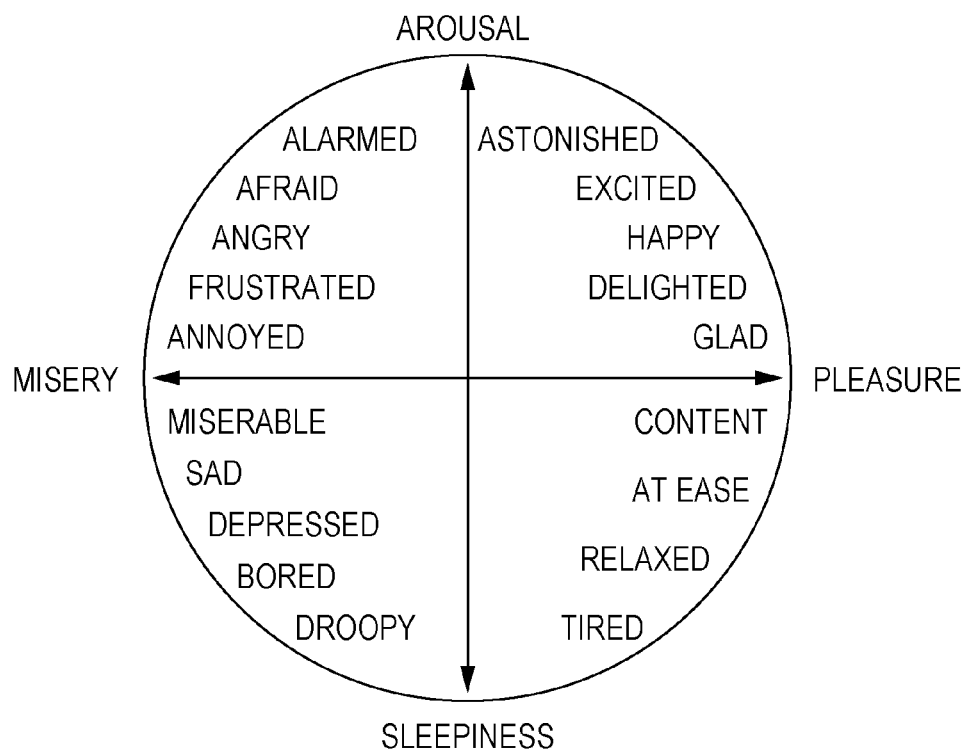
FIG. 4 is a diagram illustrating an example of Russell's circumplex model.

FIG. 3 is a block diagram illustrating an example of a detailed configuration of the physical condition estimation unit 12 illustrated in FIG. 1. FIG. 4 is a diagram illustrating an example of Russell's circumplex model.

As illustrated in FIG. 3, the physical condition estimation unit 12 includes a blood flow volume obtaining section 121 and a physical condition estimation processing section 122 and estimates a person's physical condition on the basis of the blood flow volumes of the at least two body parts measured by the blood flow measuring unit 11.

More specifically, the blood flow volume obtaining section 121 obtains the blood flow volumes of the at least two body parts measured by the blood flow measuring unit 11. The physical condition estimation processing section 122 estimates the person's physical condition on the basis of the blood flow volumes of the at least two body parts obtained by the blood flow volume obtaining section 121.

Here, it is preferable to measure blood flow volumes of the first body part, whose blood flow volume hardly varies depending on the person's physical condition, and the second body part, whose blood flow volume varies depending on the person's physical condition, as the blood flow volumes of the at least two body parts. As described above, for example, the first body part is the person's forehead, and the second body part is the person's nose, the person's lips, one of the person's hands or feet, or the person's neck, or the portions under the person's eyes. As a result, the physical condition estimation unit 12 can estimate the person's physical condition, without preliminary calibration, on the basis of the blood flow volume of the second body part relative to the blood flow volume of the first body part.

In the present embodiment, a person's physical condition refers to the person's condition other than emotions defined by Russell's circumplex model, which is a two-dimensional model illustrated in FIG. 4. The person's physical condition, therefore, may be, for example, hours of sleep, a sense of warmth and coldness, stiffness in the shoulders, a spot on the face, dryness of the skin, or the like.

If the blood flow measuring unit 11 measures blood flow volumes of the person's forehead and the portions under the person's eyes as the blood flow volumes of the at least two body parts, for example, the physical condition estimation unit 12 may estimate the hours of sleep of the person as the person's physical condition. Since a person develops dark rings under the eyes and the blood flow volume of the portions under the person's eyes decreases when the hours of sleep are short, the hours of sleep of the person of the day can be estimated from the blood flow volume of the portions under the person's eyes.

If the blood flow measuring unit 11 measures a blood flow volume of the person's forehead and a blood flow volume of at least one of the person's nose, the person's lips, and one of the person's hands or feet as the blood flow volumes of the at least two body parts, for example, the physical condition estimation unit 12 may estimate the sense of warmth and coldness of the person as the person's physical condition. Since the temperature of the person's nose becomes high relative to the temperature of the person's forehead in a hot environment and the temperature of a person's nose becomes low relative to the temperature of the person's forehead in a cold environment, the sensor of warmth and coldness of the person can be estimated from the blood flow volumes.

If the blood flow measuring unit 11 measures blood flow volumes of the person's forehead and neck as the blood flow volumes of the at least two body parts, for example, the physical condition estimation unit 12 may estimate, as the person's physical condition, whether the person's shoulders are stiff. Since a person's shoulders are (can become) stiff when the blood flow volume of the person's neck is low relative to the blood flow volume of the person's forehead, whether the person's shoulders are stiff can be estimated from the blood flow volumes. Here, a headache may be estimated as the person's physical condition instead of stiffness in the shoulders. Since a headache is likely to occur when the blood flow volume of a person's neck is low relative to the blood flow volume of the person's forehead, whether the person has a headache can be estimated from the blood flow volumes.

Although the first body part is the forehead here, the first body part may be another body part. The first body part may be any body part whose blood flow volume hardly varies depending on a person's physical condition, such as the mouth or an eyeball.

The blood flow measuring unit 11 may measure a blood flow volume of a person's face every day. In this case, the physical condition estimation unit 12 can estimate, as the person's physical condition on the basis of day-to-day variation in the blood flow volume, that a spot is likely to be formed on a part of the person's face in which the blood flow volume has decreased.

Output Control Unit 13

The output control unit 13 performs output control according to a person's physical condition estimated by the physical condition estimation unit 12.

Figure 5:
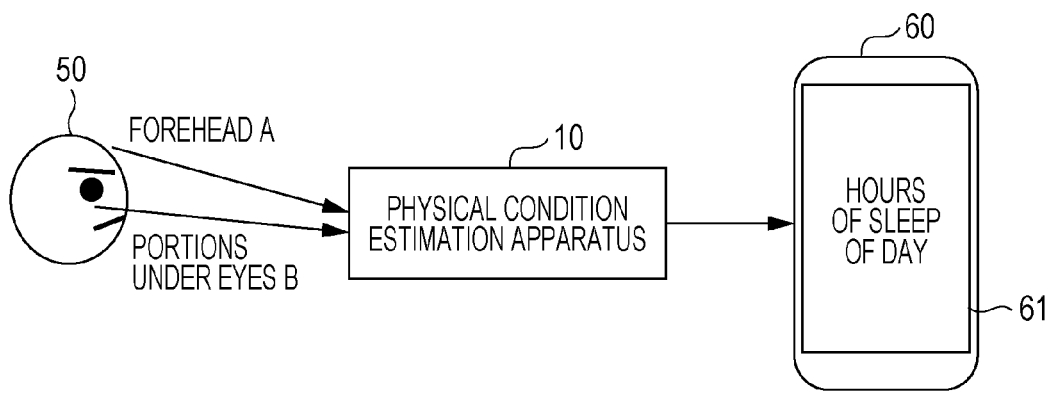
FIG. 5 is a diagram illustrating an example of output control performed by the physical condition estimation apparatus illustrated in FIG. 1.

FIG. 5 is a diagram illustrating an example of the output control performed by the physical condition estimation apparatus 10 illustrated in FIG. 1. FIG. 5 illustrates a case in which hours of sleep of the day of a person 50 estimated from the blood flow volumes of the forehead and the portions under the eyes of the person 50 are output to a screen 61 of a mobile terminal 60 owned by the person 50, such as a smartphone.

The output control performed by the physical condition estimation apparatus 10 (output control unit 13) is not limited to the example illustrated in FIG. 5, and includes output control such as display control, notification control, and device control described hereinafter.

Hours of Sleep

The output control unit 13 may predict when a person will become sleepy, for example, on the basis of the person's hours of sleep estimated by the physical condition estimation unit 12 as the person's physical condition. If the physical condition estimation apparatus 10 is installed in a vehicle, the output control unit 13 may, when the time has come, display a message urging the person to take a break on a screen of a car navigation system or a mobile terminal of the person. If the physical condition estimation apparatus 10 is installed in a space where the person stays, the output control unit 13 may, when the time has come, arouse the person by turning up lighting.

If the output control unit 13 determines that the person's accumulated hours of sleep estimated by the physical condition estimation unit 12 are short, the output control unit 13 may notify a company for which the person is working that the person needs rest.

The output control unit 13 may notify, using a mobile terminal such as a smartphone, the person of the person's hours of sleep estimated by the physical condition estimation unit 12 as the person's concentration or productivity of the day.

The output control unit 13 may determine, as the hours of sleep, information that takes into consideration hours of sleep of a plurality of days including the day estimated by the physical condition estimation unit 12, not just the hours of sleep of the day.

The output control unit 13 may set an insurance fee for the person on the basis of the person's hours of sleep of a plurality of days estimated by the physical condition estimation unit 12 and notify the person of the insurance fee. The insurance fee herein refers to a fee for life insurance, automobile insurance, or the like. Because a person is more likely to fall asleep at the wheel or contract a lifestyle-related disease when the person's hours of sleep are shorter than a certain value, an insurance fee of a person whose hours of sleep are relatively short may be set high and the person may be notified of the insurance fee.

Sense of Warmth and Coldness, Stiffness in Shoulders, Etc.

The output control unit 13 may control the air volume, the air temperature, or a wind direction of an air conditioner installed in a space where the person stays in accordance with a sense of warmth and coldness estimated by the physical condition estimation unit 12 as the person's physical condition.

If the physical condition estimation apparatus 10 is installed in a vehicle and the physical condition estimation unit 12 estimates, as a person's physical condition, that the person's shoulders are stiff, the output control unit 13 may control a seat heater included in the vehicle in such a way as to heat the person's shoulders in order to prevent or reduce the stiffness in the person's shoulders.

The output control unit 13 may notify, through a mobile terminal such as a smartphone, a person of the stiffness in the person's shoulders estimated by the physical condition estimation unit 12 as the person's concentration or productivity of the day. Furthermore, if the stiffness estimated by the physical condition estimation unit 12 is high or if the person's shoulders are often stiff, the output control unit 13 may suggest, through the mobile terminal such as a smartphone, that the person get a massage or go to a clinic, or may propose a method for reducing the stiffness. The output control unit 13 may propose another means for reducing the stiffness in the person's shoulders.

If the physical condition estimation unit 12 estimates, as a person's physical condition, that a spot is likely to appear on the person's face, the output control unit 13 may suggest, through a mobile terminal such as a smartphone, that the person get a massage, or may propose a method for reducing the likelihood of a spot. The output control unit 13 may propose another means for reducing the likelihood of a spot.

Operation of Physical Condition Estimation Apparatus 10

Figure 6:
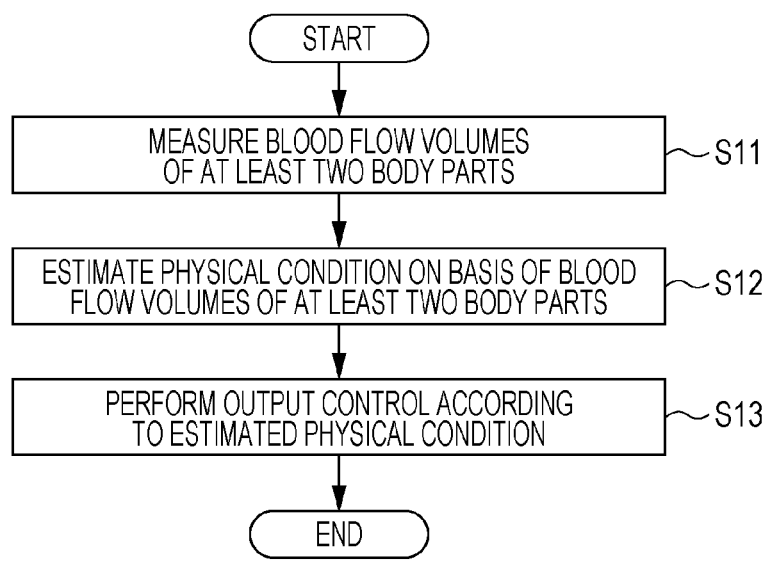
FIG. 6 is a flowchart illustrating an overview of the operation of the physical condition estimation apparatus illustrated in FIG. 1.

Next, the operation of the physical condition estimation apparatus 10 will be described with reference to FIG. 6. FIG. 6 is a flowchart illustrating an overview of the operation of the physical condition estimation apparatus 10 illustrated in FIG. 1. The operation of the physical condition estimation apparatus 10 is achieved by the computer included in the physical condition estimation apparatus 10.

First, the physical condition estimation apparatus 10 simultaneously measures the blood flow volumes of at least two body parts of a person (S11). Next, the physical condition estimation apparatus 10 estimates the person's physical condition on the basis of the blood flow volumes of the at least two body parts (S12). The physical condition estimation apparatus 10 then performs output control according to the estimated physical condition (S13).

Advantageous Effects, Etc.

As described above, with the method for estimating a physical condition according to the present embodiment and the like, a person's physical condition can be estimated without preliminary calibration even when a computer estimates the person's physical condition by measuring a blood flow volume that varies between individuals.

More specifically, in the method for estimating a physical condition and the physical condition estimation apparatus according to the present embodiment, the blood flow volumes of at least two body parts of a person, namely, for example, a body part whose blood flow volume hardly varies depending on the person's physical condition and a body part whose blood flow volume varies depending on the person's physical condition, are simultaneously measured. As a result, the person's physical condition can be estimated, without preliminary calibration, on the basis of the measured blood flow volumes of the at least two body parts.

Although a person's physical condition can be the hours of sleep, the sense of warmth and coldness, stiffness in the shoulders, a spot on the face, or dryness of the skin in the present embodiment, a person's physical condition is not limited to these. A person's physical condition may be a level of urgency at which the person wants to go to a toilet, a level of carsickness, a risk of heat shock, a risk of a vascular disorder caused by an increase in blood pressure during defecation, a level of intoxication, driving skills, a hunger level, a fatigue level, a depression level, or the like, instead. These examples will be described hereinafter as first to ninth examples.

First Example

In the first example, a case will be described in which the level of urgency at which a person wants to go to a toilet is estimated as the person's physical condition.

Figure 7:
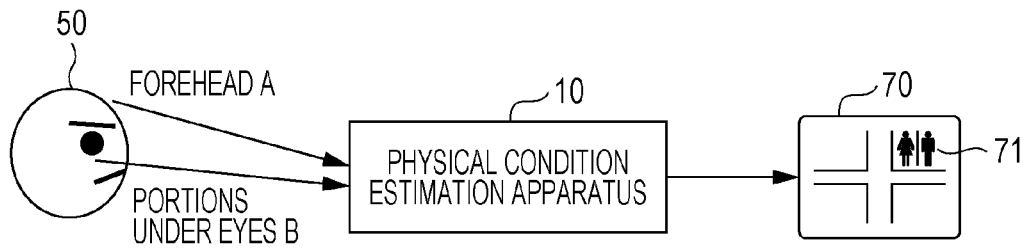
FIG. 7 is a diagram illustrating an example of output control performed by the physical condition estimation apparatus in a first example.
Figure 8:
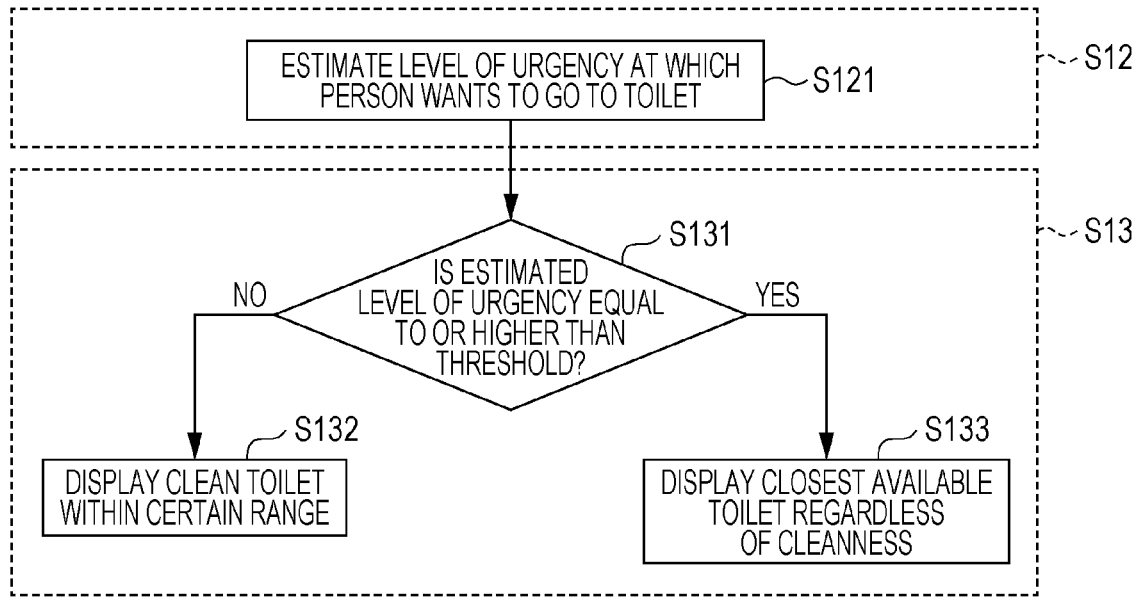
FIG. 8 is a flowchart illustrating an example of an output control method used by the physical condition estimation apparatus in the first example.

FIG. 7 is a diagram illustrating output control performed by the physical condition estimation apparatus 10 in the first example. FIG. 8 is a flowchart illustrating an example of an output control method used by the physical condition estimation apparatus 10 in the first example.

In the present example, for example, the physical condition estimation apparatus 10 measures the blood flow volumes of the person's forehead and the portions under the person's eyes as the blood flow volumes of the at least two body parts. The physical condition estimation apparatus 10 then estimates the level of urgency at which the person wants to go to a toilet as the person's physical condition on the basis of the measured blood flow volumes of the person's forehead and the portions under the person's eyes. When a person wants to go to a toilet and becomes tense, the blood flow volume of the portions under the person's eyes becomes low relative to the blood flow volume of the person's forehead. The level of urgency at which the person wants to go to a toilet, therefore, can be estimated.

If the physical condition estimation apparatus 10 in the present example is installed in a vehicle and estimates that the level of urgency at which the person wants to go to a toilet is equal to or higher than a threshold, the physical condition estimation apparatus 10 in the present example may display a public toilet 71 on a screen 70 of a car navigation system as illustrated in FIG. 7 to guide the person to the public toilet 71.

As illustrated in FIG. 8, the physical condition estimation apparatus 10 may estimate the level of urgency at which the person wants to go to a toilet (S121). If the estimated level of urgency at which the person wants to go to a toilet is lower than the threshold (NO in S131), the physical condition estimation apparatus 10 may guide the person to a clean toilet located within a certain distance (S132). On the other hand, if the level of urgency at which the person wants to go to a toilet is equal to or higher than the threshold (YES in S131), the physical condition estimation apparatus 10 may guide the person to a closest available toilet regardless of cleanness (S133).

As described above, the physical condition estimation apparatus 10 may use a different guiding method depending on the estimated level of urgency at which the person wants to go to a toilet.

The method for estimating the level of urgency at which a person wants to go to a toilet as the person's physical condition is not limited to the one based on the blood flow volumes of at least two body parts. The level of urgency at which a person wants to go to a toilet may be estimated on the basis of variation in the person's heartrate or blood pressure or the person's facial expression, instead. Since a person's heartrate and blood pressure increase and the person's facial expression changes (e.g., clenches the teeth) when the person wants to go to a toilet, the level of urgency at which the person wants to go to a toilet can be estimated. One, some, or all of the heartrate, the blood pressure, and the facial expression may be used to estimate the level of urgency at which a person wants to go to a toilet.

Second Example

In the second example, a case will be described in which the level of carsickness of a person is estimated as the person's physical condition.

Figure 9:
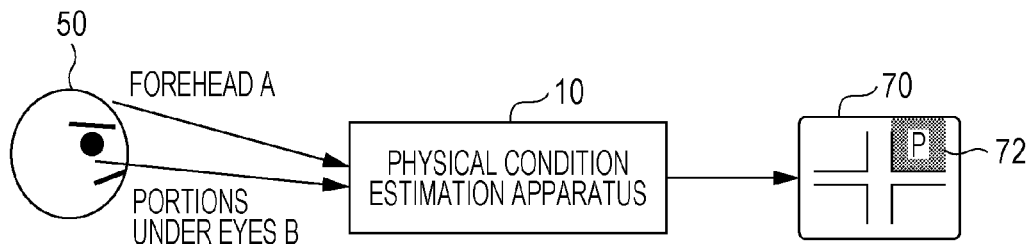
FIG. 9 is a diagram illustrating an example of output control performed by the physical condition estimation apparatus in a second example.
Figure 10:
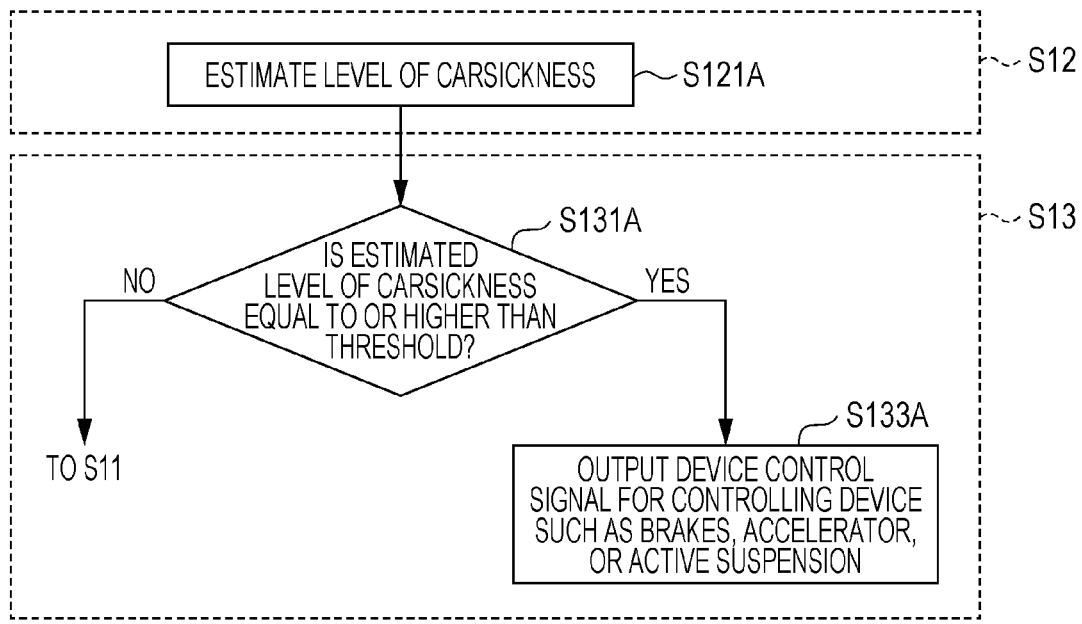
FIG. 10 is a flowchart illustrating an example of an output control method used by the physical condition estimation apparatus in the second example.

FIG. 9 is a diagram illustrating an example of output control performed by the physical condition estimation apparatus 10 in the second example. FIG. 10 is a flowchart illustrating an example of an output control method used by the physical condition estimation apparatus 10 in the second example.

In the present example, for example, the physical condition estimation apparatus 10 measures the blood flow volumes of the person's forehead and the portions under the person's eyes as the blood flow volumes of the at least two body parts. The physical condition estimation apparatus 10 then estimates the level of carsickness of the person as the person's physical condition on the basis of the measured blood flow volumes of the person's forehead and the portions under the person's eyes. Since a person gets a carsick and becomes tense, the blood flow volume of the portions under the person's eyes becomes low relative to the blood flow volume of the person's forehead. The physical condition estimation apparatus 10, therefore, can estimate the level of carsickness of the person.

If the physical condition estimation apparatus 10 is installed in a vehicle and estimates that the level of carsickness of a person is equal to or higher than a threshold, the physical condition estimation apparatus 10 may display a parking area 72 for taking a break on a screen 70 of a car navigation system to guide a driver to the parking area 72 as illustrated in FIG. 9. The method for notifying the driver of the person's physical condition, needless to say, is not limited to this. For example, the physical condition estimation apparatus 10 may display the person's physical condition on the screen 70 of the car navigation system or an instrument panel or output a speech sound through a mobile terminal of the driver or a vehicle speaker, in order to notify the driver of the person's physical condition. Any other method may be used.

As illustrated in FIG. 10, for example, the physical condition estimation apparatus 10 may estimate the level of carsickness of the person (S121A). If the estimated level of carsickness of the person is lower than a threshold (NO in S131A), the process may return to S11 and the physical condition estimation apparatus 10 may estimate the level of carsickness of the person a certain period of time later. On the other hand, if the estimated level of carsickness of the person is equal to or higher than the threshold (YES in S131A), a device control signal for controlling a vehicle device such as brakes, an accelerator, or an active suspension may be output (S133A).

As a result, the sensitivity of the accelerator or the brakes can be reduced in order to suppress a sudden start or stop and reduce the level of carsickness of the person, or the active suspension can be made softer in order to reduce vibration applied to the person's body. By controlling a device in this manner, the person can be prevented from throwing up in the vehicle or an increase in the level of carsickness can be suppressed, even if the person is a child or hesitates to tell the driver that he/she is carsick. If the vehicle is a taxi, the driver can allow the person to get out before the person throws up, or decline to pick up the person.

The method for estimating the level of carsickness of a person as the person's physical condition is not limited to the one based on the blood flow volumes of at least two body parts. The level of carsickness may be estimated on the basis of a person's facial expression, heartrate, or blood pressure. Since a person's face becomes pale or looks unwell or a temporal correlation ($\rho$max) between the person's heartrate and blood pressure decreases when the person is carsick, the level of carsickness of the person can be estimated. The level of carsickness of the person may be estimated using $\rho$max and/or the facial expression.

Third Example

In the third example, a case will be described in which the risk of heat shock of a person is estimated as the person's physical condition. Heat shock herein refers to a vascular disorder such as a faint, a myocardial infarction, or a cerebral infarction caused by a sudden change in blood pressure. Heat shock often occurs when a person undresses in a cold changing room before bathing and the blood pressure suddenly increases or when a person takes a hot bath and the blood pressure suddenly increases.

In the present example, for example, the physical condition estimation apparatus 10 measures the blood flow volumes of the person's forehead and the portions under the person's eyes as the blood flow volumes of the at least two body parts. The physical condition estimation apparatus 10 then estimates the risk of heat shock of the person as the person's physical condition on the basis of the measured blood flow volumes of the person's forehead and the portions under the person's eyes. Since the blood flow volume of the portions under a person's eyes is low relative to the blood flow volume of the person's forehead in a cold environment and the blood flow volume of the portions under the person's eyes is high relative to the blood flow volume of the person's forehead in a hot environment, the risk of heat shock of the person can be estimated.

Figure 11:
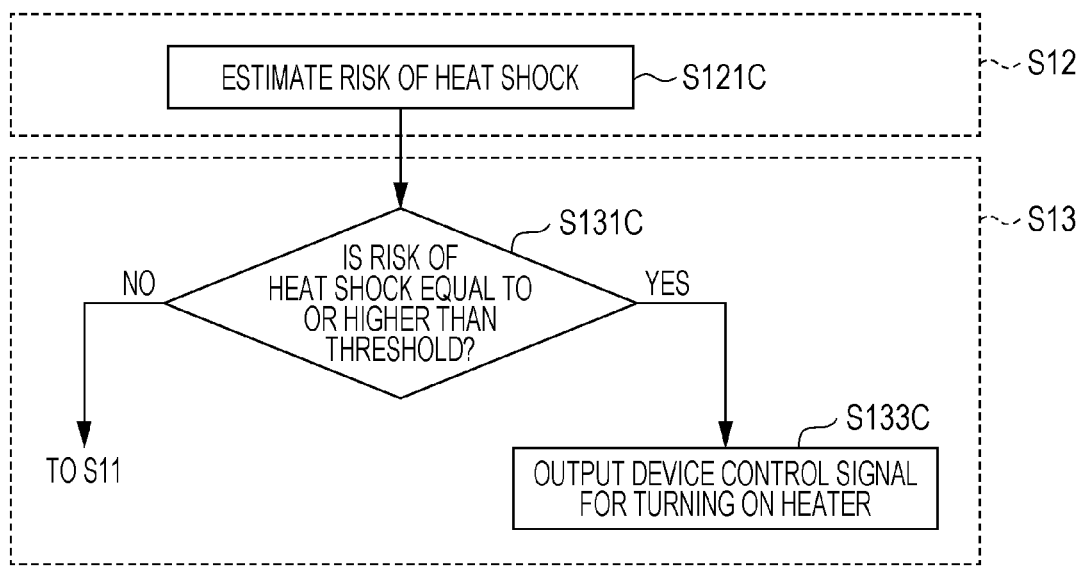
FIG. 11 is a flowchart illustrating an example of an output control method used by the physical condition estimation apparatus in a third example.

FIG. 11 is a flowchart illustrating an example of an output control method used by the physical condition estimation apparatus 10 in the third example.

As illustrated in FIG. 11, for example, the physical condition estimation apparatus 10 may estimate the risk of heat shock of a person (S121C). If the estimated risk of heat shock of the person is lower than a threshold (NO in S131C), the process may return to S11 and the physical condition estimation apparatus 10 may estimate the risk of heat shock of the person a certain period of time later. On the other hand, if the estimated risk of heat shock of the person is equal to or higher than the threshold (YES in S131C), a device control signal including an instruction to turn on a heater may be output in order to increase temperature around the person (S133C).

As a result, a sudden change in the person's blood pressure can be suppressed, and heat shock can be prevented.

The output control method used by the physical condition estimation apparatus 10 when the estimated risk of heat shock of the person is equal to or higher than the threshold is not limited to this. If the person is in a changing room or a toilet, for example, the person may be notified of the risk and urged to use a heater. If the estimated risk of heat shock of the person is equal to or higher than the threshold when the person takes a bath, for example, the physical condition estimation apparatus 10 may output a device control signal including an instruction to add water to the bath. As a result, the temperature of the bath can be decreased, thereby suppressing a sudden change in the person's blood pressure.

The method for estimating the risk of heat shock of a person as the person's physical condition is not limited to the one based on the blood flow volumes of at least two body parts. The risk of heat shock of a person may be estimated on the basis of the person's blood pressure, instead. If the person's blood pressure can be constantly measured and has become equal to or higher than a certain value, for example, the physical condition estimation apparatus 10 can estimate that the risk of heat shock is high.

Here, a plurality of thresholds may be provided instead of the certain value, and the risk of heat shock may be estimated stepwise. The threshold(s) of blood pressure used to determine the risk of heat shock may be adjusted on the basis of a degree of arteriosclerosis. The degree of arteriosclerosis can be estimated from pulse pressure (highest blood pressure and lowest blood pressure) or a pulse wave propagation time. Any other method may be used.

The threshold(s) of blood pressure may be adjusted on the basis of age or a water content level inside the body, instead of the degree of arteriosclerosis. This is because when the water content level inside the body is small, the blood pressure sharply changes, which can lead to heat shock. Another method may be used to adjust the threshold(s) of blood pressure, insofar as the risk of heat shock can be estimated.

The degree of arteriosclerosis may be manually input on the basis of a result of a medical examination, instead of being detected in a noncontact manner. The age, too, may be manually input.

If the blood pressure can be constantly measured, a warning or a notification may be issued in accordance with the degree of arteriosclerosis or the water content level. Changes in the person's blood pressure may be displayed to the person.

Fourth Example

In the fourth example, a case will be described in which a person's risk of a vascular disorder caused by an increase in blood pressure during defecation is estimated as the person's physical condition. During defecation, a person pushes down hard, and the person's blood pressure increases. This might cause a vascular disorder such as a faint, a myocardial infarction, or a cerebral infarction.

In the present example, for example, the physical condition estimation apparatus 10 measures the blood flow volumes of the person's forehead and the portions under the person's eyes as the blood flow volumes of the at least two body parts. The physical condition estimation apparatus 10 then estimates the risk of a vascular disorder caused by an increase in the blood pressure during defecation as the person's physical condition on the basis of the measured blood flow volumes of the person's forehead and the portions under the person's eyes. Since the blood flow volume of the portions under a person's eyes becomes high relative to the blood flow volume of the person's forehead during defecation, the risk of a vascular disorder caused by an increase in the blood pressure during defecation can be estimated.

If estimating that the risk of a vascular disorder caused by an increase in the blood pressure during defecation is equal to or higher than a certain value, the physical condition estimation apparatus 10 in the present example may notify the person of the result of the estimation to urge the person not to push down very hard or may control a shower toilet in such a way as to spray water around the person's anus to allow the person not to push down very hard.

As a result, a sudden change in the person's blood pressure can be suppressed, and a vascular disorder can be prevented.

The method for estimating the risk of a vascular disorder caused by an increase in the blood pressure during defecation as a person's physical condition is not limited to the one based on the blood flow volumes of at least two body parts. The risk of a vascular disorder caused by an increase in the blood pressure during defecation may be estimated from a person's blood pressure, instead. If the person's blood pressure can be constantly measured and has become equal to or higher than a certain value, for example, the physical condition estimation apparatus 10 can estimate that the risk of a vascular disorder caused by an increase in the blood pressure during defecation is high.

Here, a plurality of thresholds may be provided instead of the certain value, and the risk of a vascular disorder caused by an increase in the blood pressure during defecation may be estimated stepwise. The threshold(s) of blood pressure used to determine the risk of caused by an increase in the blood pressure during defecation may be adjusted on the basis of the degree of arteriosclerosis. The degree of arteriosclerosis can be estimated from pulse pressure (highest blood pressure and lowest blood pressure) or a pulse wave propagation time. Any other method may be used.

The threshold(s) of blood pressure may be adjusted on the basis of the age or the water content level inside the body, instead of the degree of arteriosclerosis. This is because when the water content level inside the body is low, the blood pressure sharply changes, which can lead to a vascular disorder. Another method may be used to adjust the threshold(s) of blood pressure, insofar as the risk of a vascular disorder caused by an increase in the blood pressure during defecation can be estimated.

The degree of arteriosclerosis may be manually input on the basis of a result of a medical examination, instead of being detected in a noncontact manner. The age, too, may be manually input.

If the blood pressure can be constantly measured, a warning or a notification may be issued in accordance with the degree of arteriosclerosis or the water content level. Changes in the person's blood pressure may be displayed to the person.

Fifth Example

In the fifth example, a case will be described in which the level of intoxication of a person is estimated as the person's physical condition.

In the present example, for example, the physical condition estimation apparatus 10 measures the blood flow volumes of the person's forehead and the portions under the person's eyes as the blood flow volumes of the at least two body parts. The physical condition estimation apparatus 10 then estimates the level of intoxication of the person as the person's physical condition on the basis of the measured blood flow volumes of the person's forehead and the portions under the person's eyes. Since the blood flow volume of the portions under a person's eyes becomes high relative to the blood flow volume of the person's forehead when the person is intoxicated and the blood flow volume of the portions under the person's eyes becomes low relative to the blood flow volume of the person's forehead when the person is sick due to intoxication, the level of intoxication of the person can be estimated.

If the physical condition estimation apparatus 10 in the present example is installed in a vehicle and estimates that the level of intoxication of the person is equal to or higher than a certain value, that is, if the person is intoxicated, the physical condition estimation apparatus 10 may control an engine of the vehicle such that the engine does not start (device control). As a result, an intoxicated person is prevented from driving the vehicle.

If the physical condition estimation apparatus 10 in the present example estimates that the level of the intoxication of the person is equal to or higher than the certain value, that is, if the person has drunk too much, the physical condition estimation apparatus 10 may notify the person of the result of the estimation or display the level of intoxication of the person to the person. As a result, the person can understand the level of intoxication thereof and it becomes possible to prevent the person from drinking too much again.

The method for estimating the level of intoxication of a person as the person's physical condition is not limited to the one based on the blood flow volumes of at least two body parts. The level of intoxication of a person may be estimated on the basis of the person's facial expression, heartrate, blood pressure, blood flow, or exhaled air, instead. Since, when a person gets intoxicated, the person's line of sight becomes unstable, the person's circulation of the blood improves and the person's heartrate increases, the person's face turns red, the person becomes relaxed and the person's blood pressure decreases, and the alcohol concentration of the person's exhaled air increases, the level of intoxication of the person can be estimated. One, some, or all of these pieces of information may be used to estimate the level of intoxication of a person.

Sixth Example

In the sixth example, a case will be described in which a person's driving skills are estimated as the person's physical condition.

In the present example, for example, the physical condition estimation apparatus 10 measures the blood flow volumes of the person's forehead and the portions under the person's eyes as the blood flow volumes of the at least two body parts. The physical condition estimation apparatus 10 then estimates the person's driving skills as the person's physical condition on the basis of the measured blood flow volumes of the person's forehead and the portions under the person's eyes. Since a person does not become tense and the blood flow volume of the portions under the person's eyes becomes high relative to the blood flow volume of the person's forehead when the person's driving skills are high and a person becomes tense and the blood flow volume of the portions under the person's eyes becomes low relative to the blood flow volume of the person's forehead when the person's driving skills are low, the person's driving skills can be estimated.

If the physical condition estimation apparatus 10 in the present example estimates that the person's driving skills are lower than a certain value, that is, if the person is tense during driving, the physical condition estimation apparatus 10 may increase the sensitivity of brakes to keep a distance to a vehicle ahead or may decrease the sensitivity of an accelerator to keep the speed of the vehicle low. As a result, the person becomes relaxed during driving even if the person's driving skills are low and the person has been tense.

The method for estimating a person's driving skills as the person's physical condition is not limited to the one based on the blood flow volumes of at least two body parts. A person's driving skills may be estimated from the person's facial expression or variation in the person's heartrate. Since whether a person is relaxed can be estimated from the person's facial expression and variation in the person's heartrate becomes small when the person is tense during driving and large when the person is relaxed, the person's driving skills can be estimated. One, some, or all of these pieces of information may be used to estimate a person's driving skills.

If the physical condition estimation apparatus 10 in the present example is installed in a vehicle and estimates a person's physical condition on the basis of the person's facial expression, the physical condition estimation apparatus 10 may estimate a person's fear as the person's physical condition. For example, the physical condition estimation apparatus 10 in the present example estimates, on the basis of a person's facial expression, whether the person, who is inside the vehicle, is afraid during automated driving. If the physical condition estimation apparatus 10 estimates that the person is afraid, that is, if the person is tense (does not trust the automated driving), the physical condition estimation apparatus 10 may control a vehicle device such that a distance to a vehicle ahead increases and the speed of the vehicle decreases. As a result, the person in the vehicle feels safe.

If the physical condition estimation apparatus 10 in the present example detects, on the basis of a person's facial expression, that the person is looking out over scenery, the physical condition estimation apparatus 10 may control a vehicle device such that the speed of the vehicle decreases. As a result, the person can enjoy the scenery.

Seventh Example

In the seventh example, a case will be described in which a person's hunger level is estimated as the person's physical condition.

In the present example, for example, the physical condition estimation apparatus 10 measures the blood flow volumes of the person's forehead and the portions under the person's eyes as the blood flow volumes of the at least two body parts. The physical condition estimation apparatus 10 then estimates the person's hunger level as the person's physical condition on the basis of the measured blood flow volumes of the person's forehead and the portions under the person's eyes. Since the blood flow volume of the portions under a person's eyes becomes low relative to the blood flow volume of the person's forehead when the person's hunger level is high and the person is stressed, the person's hunger level can be estimated.

If the physical condition estimation apparatus 10 in the present example is installed in an office and estimates that a person's hunger level is equal to or higher than a certain value, that is, that the person is hungry, the physical condition estimation apparatus 10 may control lighting such that a blue component included in the light increases (device control). This is because a person becomes less hungry when seeing blue light.

If the physical condition estimation apparatus 10 in the present example is installed in a vehicle and estimates that a person's hunger level is equal to or higher than the certain value, that is, that the person is hungry, the physical condition estimation apparatus 10 in the present example may display a nearby restaurant on a screen of a car navigation system and guide the person to the restaurant.

The method for estimating a person's hunger level as the person's physical condition is not limited to the one based on the blood flow volumes of at least two body parts. A person's hunger level may be estimated from the person's blood sugar level or exhaled air or sound from the person's abdomen, instead. Since, when the person is hungry, a person's blood sugar level decreases, the amount of acetone included in the person's exhaled air increases, and the person's gastrointestinal activity increases, the person's hunger level can be estimated. One, some, or all of these pieces of information may be used to estimate a person's hunger level.

Eighth Example

In the eighth example, a case will be described in which a person's fatigue level is estimated as the person's physical condition.

In the present example, for example, the physical condition estimation apparatus 10 measures the blood flow volumes of the person's forehead and the portions under the person's eyes as the blood flow volumes of the at least two body parts. The physical condition estimation apparatus 10 then estimates the person's fatigue level as the person's physical condition on the basis of the measured blood flow volumes of the person's forehead and the portions under the person's eyes. Since the blood flow volume of the portions under the person's eyes becomes low relative to the blood flow volume of the person's forehead when the person is fatigued and stressed, the person's fatigue level can be estimated.

If the physical condition estimation apparatus 10 in the present example is installed in a vehicle and estimates that a person's fatigue level is equal to or higher than a certain value, the physical condition estimation apparatus 10 may control a vehicle device in such a way as to urge the person to take a break or switch to automated driving in order to suppress the fatigue of the person, who is a driver.

The method for estimating a person's fatigue level as the person's physical condition is not limited to the one based on the blood flow volumes of at least two body parts. A person's fatigue level may be estimated from the person's facial expression or oxygen saturation or lactic acid concentration in blood flow, instead. Since, when a person is fatigued, the oxygen saturation in blood flow decreases, the lactic acid concentration in the blood flow increases, and the person's face looks fatigued, the person's fatigue level can be estimated. One, some, or all of these pieces of information may be used to estimate a person's fatigue level.

Ninth Example

In the ninth example, a case will be described in which a person's depression level is estimated as the person's physical condition.

In the present example, for example, the physical condition estimation apparatus 10 measures the blood flow volumes of the person's forehead and the portions under the person's eyes as the blood flow volumes of the at least two body parts. The physical condition estimation apparatus 10 then estimates the person's depression level as the person's physical condition on the basis of the measured blood flow volumes of the person's forehead and the portions under the person's eyes. Since the blood flow volume of the portions under a person's eyes becomes low relative to the blood flow volume of the person's forehead when the person is depressed and stressed, the person's depression level can be estimated.

If the physical condition estimation apparatus 10 in the present example estimates that a person's depression level is equal to or higher than a certain value, that is, that the person is depressed, the physical condition estimation apparatus 10 may control lighting in a room. By controlling the lighting in the room such that, for example, the lighting becomes bright in the morning and dim at night, the person's circadian rhythm can be adjusted and the person becomes less depressed. If the physical condition estimation apparatus 10 in the present example estimates that a person's depression level is equal to or higher than the certain value, that is, that the person is depressed, the physical condition estimation apparatus 10 may control an audio system such that the audio system plays back encouraging songs in the morning and relaxing songs at night.

The method for estimating a person's depression level as the person's physical condition is not limited to the one based on the blood flow volumes of at least two body parts. A person's depression level may be estimated from the person's facial expression or heartrate, instead. Since a period of time for which a person's parasympathetic nervous system remains active in a day decreases when the person is depressed, and since the period of time for which the person's parasympathetic nervous system remains active can be identified by checking temporal variation in the person's heartrate, the person's depression level can be estimated. In addition, it is known that when a person is depressed, facial expressions unique to a depressed person (e.g., a vacuous expression) are observed. Whether a person is depressed, therefore, can be estimated from the person's facial expression at a certain timing such as rising or a change in the person's facial expression at a time when a certain image is displayed. One, some, or all of these pieces of information may be used to estimate a person's depression level.

Second Embodiment

Although a person's physical condition is estimated on the basis of physiological values such as the blood flow volumes of at least two body parts of the person in the first embodiment, the method for estimating a person's physical condition is not limited to this. A person's physical condition may be estimated on the basis of the person's physiological values and then corrected on the basis of the person's emotion at a time when the physiological values are obtained. This case will be described hereinafter as a second embodiment.

Configuration of Physical Condition Estimation Apparatus

Figure 12:
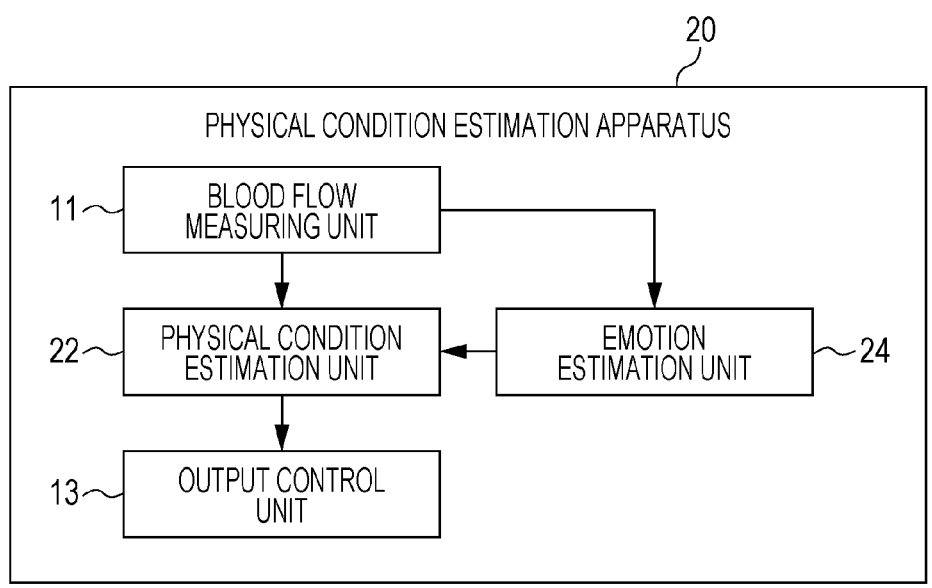
FIG. 12 is a block diagram illustrating the configuration of a physical condition estimation apparatus according to a second embodiment.

FIG. 12 is a block diagram illustrating the configuration of a physical condition estimation apparatus 20 according to the second embodiment. The same components as those illustrated in FIG. 1 and other drawings are given the same reference numerals, and detailed description thereof is omitted.

As illustrated in FIG. 12, the physical condition estimation apparatus 20 includes the blood flow measuring unit 11, a physical condition estimation unit 22, the output control unit 13, and an emotion estimation unit 24. The physical condition estimation apparatus 20 is implemented as a computer or the like. The physical condition estimation apparatus 20 illustrated in FIG. 12 is different from the physical condition estimation apparatus 10 according to the first embodiment in that the physical condition estimation apparatus 20 includes the emotion estimation unit 24 and the configuration of the physical estimation unit 22 is different from that of the physical condition estimation unit 12.

Emotion Estimation Unit 24

The emotion estimation unit 24 estimates a person's emotion on the basis of the person's physiological value. More specifically, the emotion estimation unit 24 estimates a person's emotion using Russell's circumplex model illustrated in FIG. 4 on the basis of the person's physiological value. The physiological value is data regarding a function of a living body and may indicate at least, for example, complexion, a heartrate, variation in the heartrate, a ratio of a low-frequency (LF) component to a high frequency (HF) component (LF/HF) of the variation in the heartrate, R-R intervals, a pulse wave, variation in the pulse wave, a brain wave, a respiratory rate, respiratory volume, blood flow, variation in the blood flow, blood pressure, variation in the blood pressure, oxygen saturation ($SpO_2$), the movement of a body part, the movement of a body muscle, the movement of a facial muscle, body temperature, skin temperature, skin conductance, skin resistance, the coarseness of the skin, the shininess of the skin, the amount of sweat, or a sweating rate. The movement of a body part may be, for example, blinking frequency, a blinking rate, or the like.

That is, the emotion estimation unit 24 may estimate a person's emotion, such as an arousal level of the person, on the basis of one of the blood flow volumes of the at least two body parts measured by the blood flow measuring unit 11 as the person's physiological value. Alternatively, the emotion estimation unit 24 may estimate a person's emotion, such as the arousal level of the person, on the basis of a blood flow volume of a body part different from the blood flow volumes of the at least two body parts measured by the blood flow measuring unit 11 as the person's physiological value. Alternatively, the emotion estimation unit 24 may estimate, as a person's physiological value, the person's emotion on the basis of, for example, a physiological value such as facial expression, the heartrate, respiration, the pulse wave, the blood pressure, or any combination thereof.

Alternatively, the emotion estimation unit 24 may estimate a person's emotion by determining a position along a pleasure axis on the basis of the person's facial expression and a position along an arousal axis on the basis of the person's physiological value such as the blood flow, heartbeats, the respiration, the pulse wave, or the blood pressure using Russell's circumplex model illustrated in FIG. 4. This case will be described hereinafter.

Figure 13:
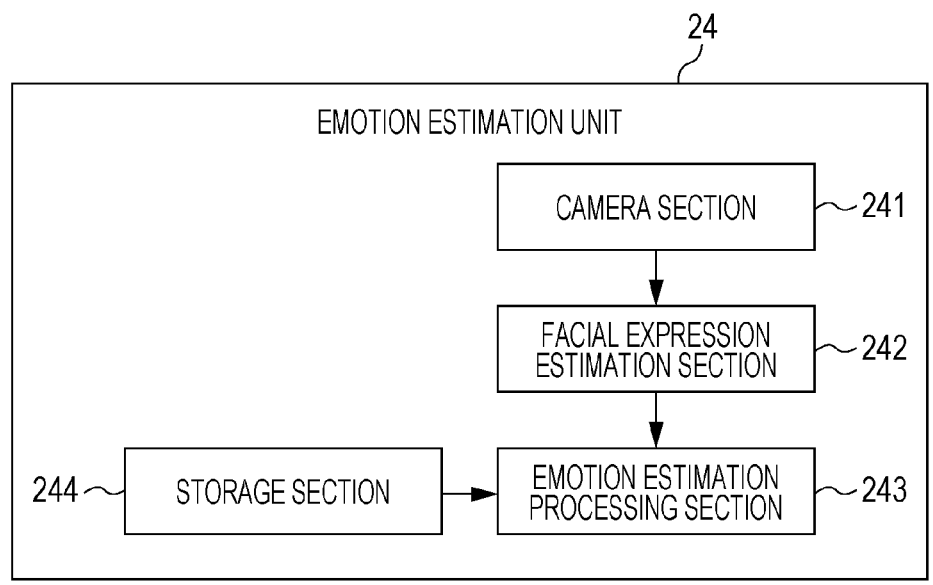
FIG. 13 is a block diagram illustrating an example of a detailed configuration of an emotion estimation unit illustrated in FIG. 12.
Figure 14A:
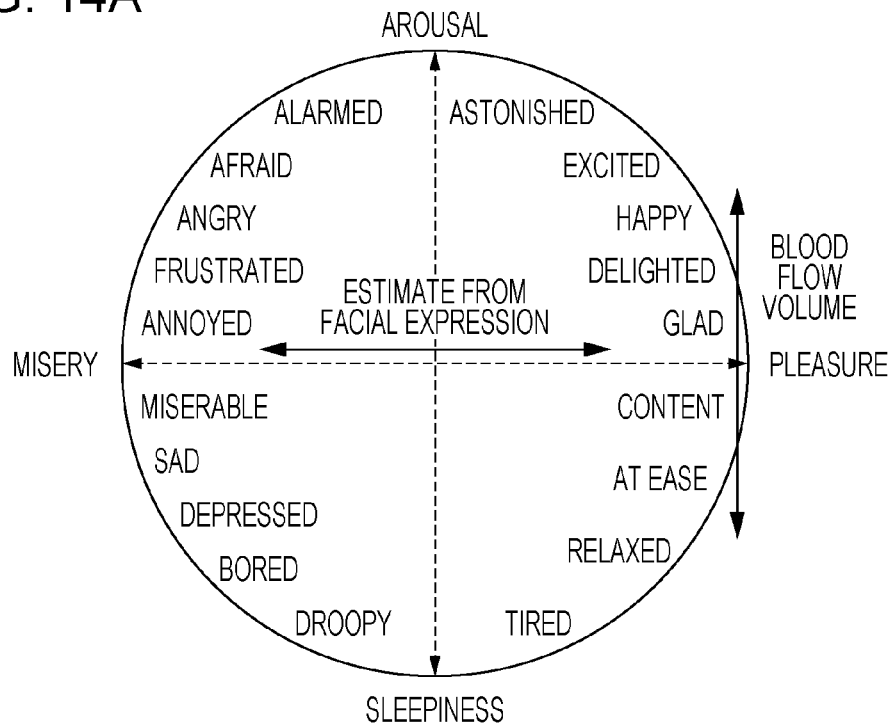
FIG. 14A is a diagram illustrating an example of a mode in which the emotion estimation unit illustrated in FIG. 12 uses Russell's circumplex model.
Figure 14B:
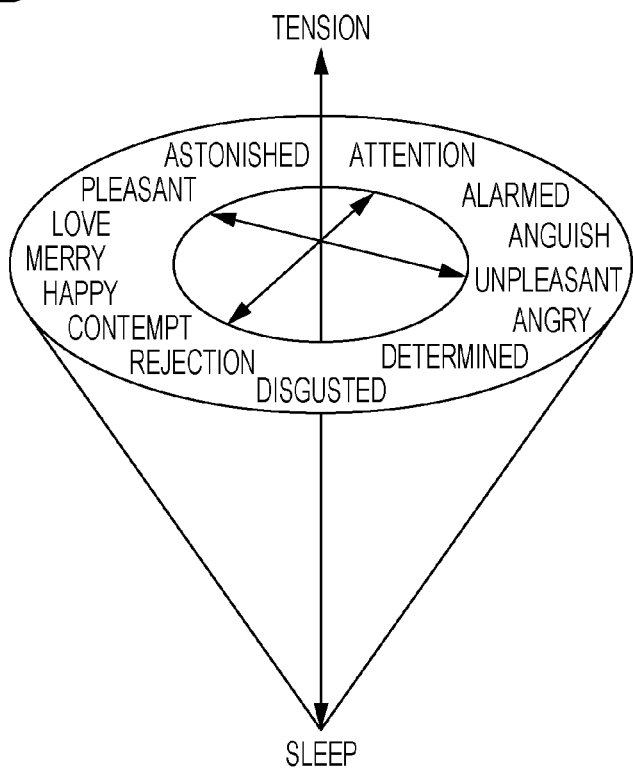
FIG. 14B is a diagram illustrating an example of Schlosberg's conic model used by the emotion estimation unit illustrated in FIG. 12.

FIG. 13 is a block diagram illustrating an example of a detailed configuration of the emotion estimation unit 24 illustrated in FIG. 12. FIG. 14A is a diagram illustrating an example of a mode in which the emotion estimation unit 24 illustrated in FIG. 12 uses Russell's circumplex model. FIG. 14B is a diagram illustrating an example of Schlosberg's conic model used by the emotion estimation unit 24 illustrated in FIG. 12.

As illustrated in FIG. 13, the emotion estimation unit 24 includes a camera section 241, a facial expression estimation section 242, an emotion estimation processing section 243, and a storage section 244.

A person experiences various emotions such as pleasure and astonishment. In Russell's circumplex model illustrated in FIG. 4, various emotions experienced by a person are mapped on a plane defined by a pleasure axis and an arousal axis. Russell's circumplex model illustrated in FIG. 4 indicates that various emotions experienced by a person can be mapped in a circle. It might be difficult to determine a position along the arousal axis on the basis of a person's facial expression, but the position can be calculated from the person's physiological value described above, such as the person's heartrate. A position along the pleasure axis, on the other hand, may be calculated from a person's facial expression. In doing so, the person's emotion can be estimated more accurately than when the person's emotion is estimated only on the basis of the person's facial expression and physiological value.

The storage section 244 stores, for example, data corresponding to Russell's circumplex model illustrated in FIG. 14.

The camera section 241 captures an image of the entirety of a person's face. The facial expression estimation section 242 estimates the person's facial expression on the basis of the image of the person's face captured by the camera section 241.

The emotion estimation processing section 243 refers, for example, to the data corresponding to Russell's circumplex model illustrated in FIG. 14 stored in the storage section 244. The emotion estimation processing section 243 may determine a person's emotion by determining a position along the pleasure axis on the basis of the person's facial expression estimated by the facial expression estimation section 242 and a position along the arousal axis on the basis of the blood flow volumes of the at least two body parts measured by the blood flow measuring unit 11. Alternatively, as described above, the emotion estimation processing section 243 may determine a position along the arousal axis on the basis of physiological data such as the heartbeats, the respiration, the pulse wave, or the blood pressure. For example, the emotion estimation processing section 243 may determine a position along the arousal axis by estimating the person's heartrate from slight changes in the person's complexion estimated by the facial expression estimation section 242. An emotion may be calculated not only when an estimated physical condition is corrected but also when only the emotion is obtained.

Although a case in which an emotion is estimated using Russell's circumplex model has been described, another model may be used, instead. In Schlosberg's conic model illustrated in FIG. 14B, for example, a tension level, which indicates whether a person is tense or sleepy, may be calculated from a physiological value, and whether or not the person is pleasant and whether or not the person is paying attention, which are indicated in a circle, may be calculated from the person's facial expression. Alternatively, whether or not the person is paying attention may also be calculated from a physiological value. In doing so, an emotion can be estimated more accurately.

Physical Condition Estimation Unit 22

Figure 15:
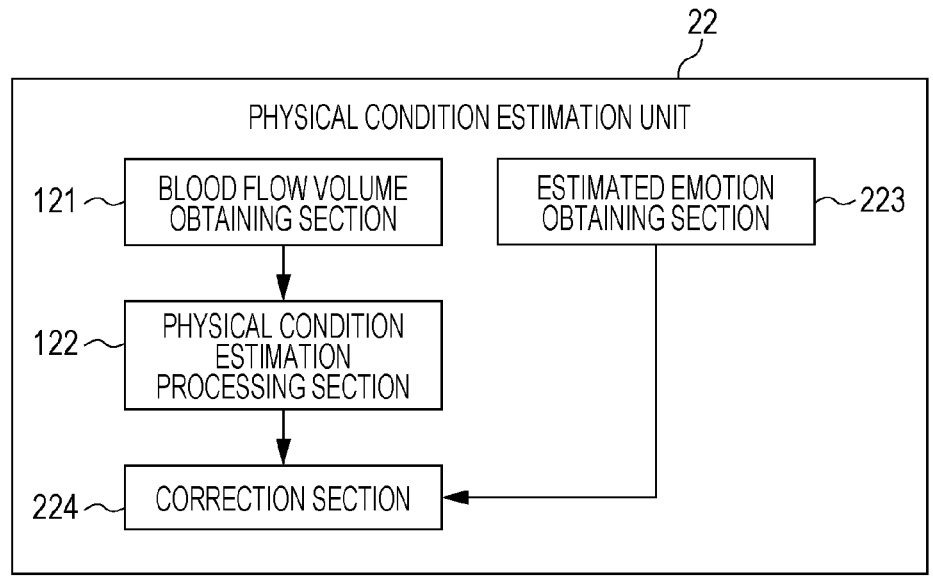
FIG. 15 is a block diagram illustrating an example of a detailed configuration of the physical condition estimation unit illustrated in FIG. 12.

FIG. 15 is a block diagram illustrating an example of a detailed configuration of the physical condition estimation unit 22 illustrated in FIG. 12. The same components as those illustrated in FIG. 3 are given the same reference numerals, and detailed description thereof is omitted.

As illustrated in FIG. 15, the physical condition estimation unit 22 includes the blood flow volume obtaining section 121, the physical condition estimation processing section 122, an estimated emotion obtaining section 223, and a correction section 224. The physical condition estimation unit 22 estimates a person's physical condition on the basis of the blood flow volumes of the at least two body parts measured by the blood flow measuring unit 11. The physical condition estimation unit 22 illustrated in FIG. 15 is different from the physical condition estimation unit 12 according to the first embodiment illustrated in FIG. 3 in that the physical condition estimation unit 22 includes the estimated emotion obtaining section 223 and the estimated emotion obtaining section 223.

More specifically, the estimated emotion obtaining section 223 obtains a person's emotion estimated by the emotion estimation unit 24. The correction section 224 corrects the person's physical condition estimated by the physical condition estimation processing section 122 on the basis of the person's emotion estimated by the emotion estimation unit 24.

A case will be described in which, for example, the blood flow volume measurement processing section 112 has estimated a certain level of stiffness in the shoulders as a person's physical condition and the emotion estimation unit 24 has estimated "excited" as the person's emotion. Because "excited" contributes to increasing the blood flow volume of the person and reducing the stiffness in the shoulders, the correction section 224 corrects the person's physical condition to a level of stiffness in the shoulders lower than the certain level. The physical condition estimation unit 22 can thus obtain a result of estimation by correcting a person's physical condition on the basis of the person's emotion.

Operation of Physical Condition Estimation Apparatus 20

Figure 16:
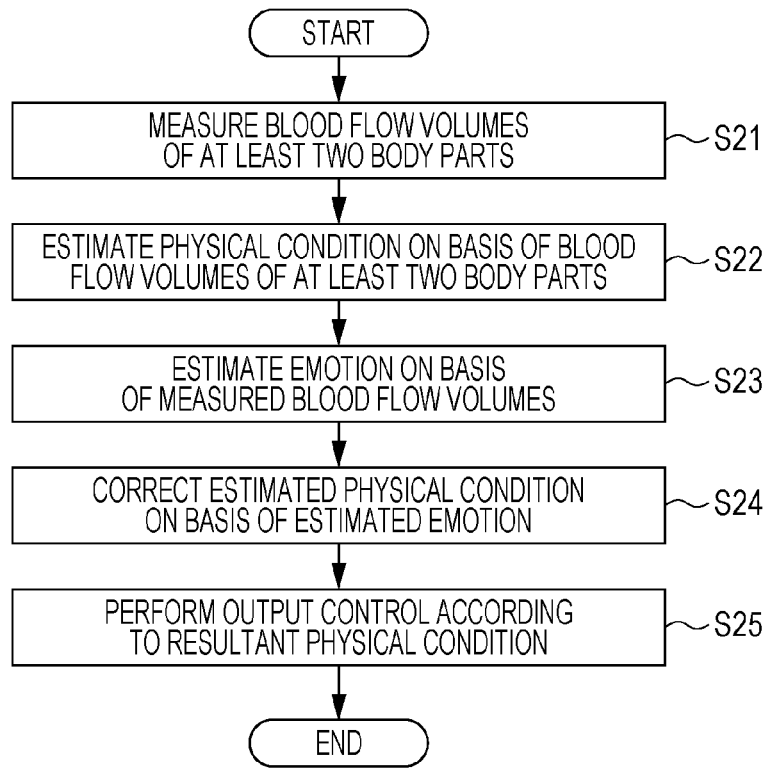
FIG. 16 is a flowchart illustrating an overview of the operation of the physical condition estimation apparatus illustrated in FIG. 12.

Next, the operation of the physical condition estimation apparatus 20 will be described with reference to FIG. 16. FIG. 16 is a flowchart illustrating an overview of the operation of the physical condition estimation apparatus 20 illustrated in FIG. 12. The operation of the physical condition estimation apparatus 20 is achieved by the computer included in the physical condition estimation apparatus 20.

First, the physical condition estimation apparatus 20 simultaneously measures the blood flow volumes of at least two body parts of a person (S21). Next, the physical condition estimation apparatus 20 estimates the person's physical condition on the basis of the measured blood flow volumes of the at least two body parts (S22). Next, the physical condition estimation apparatus 20 estimates the person's emotion on the basis of a blood flow volume of at least one body part (S23). The blood flow volume of the at least one body part for estimating the person's emotion may be the blood flow volume of at least one of the at least two body parts measured to estimate the person's physical condition or may be another body part. Next, the physical condition estimation apparatus 20 corrects the person's physical condition estimated in S22 on the basis of the person's emotion estimated in S23 (S24). The physical condition estimation apparatus 20 then performs output control according to the resultant physical condition (S25).

Advantageous Effects, Etc.

As described above, with the method for estimating a physical condition according to the present embodiment and the like, a person's physical condition can be estimated without preliminary calibration even when a computer estimates the person's physical condition by measuring a blood flow volume that varies between individuals. Furthermore, with the method for estimating a physical condition according to the present embodiment and the like, the estimated physical condition can be corrected on the basis of the person's emotion. The person's physical condition that takes into consideration the person's emotion, therefore, can be estimated.

A case will be described hereinafter, as an example, in which a physical condition to be estimated is a level of stiffness in the shoulders and an emotion to be estimated is a level of excitement.

EXAMPLE

Figure 17:
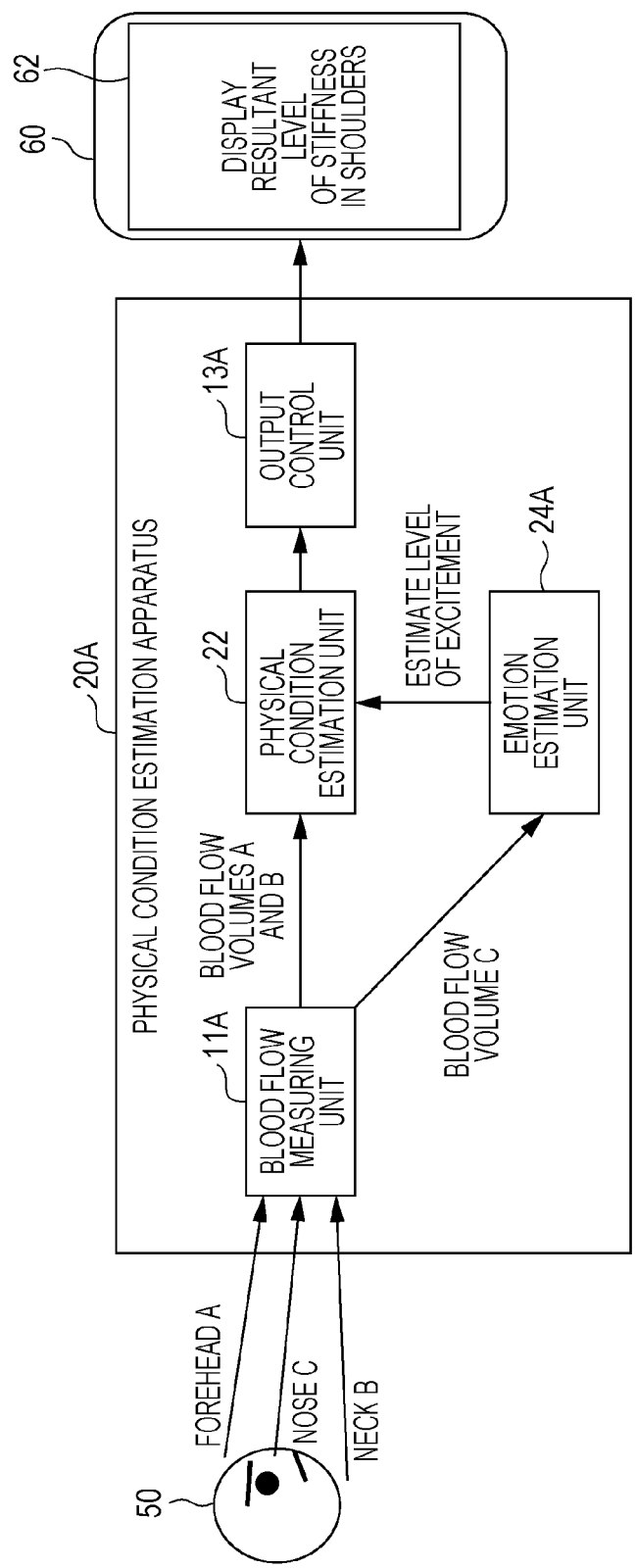
FIG. 17 is a diagram illustrating an example of output control performed by a physical condition estimation apparatus in an example of the second embodiment.

FIG. 17 is a diagram illustrating an example of output control performed by a physical condition estimation apparatus 20A in an example of the second embodiment.

In the present example, for example, a blood flow measuring unit 11A measures a blood flow volume A of a forehead of the person 50, a blood flow volume B of a neck B of the person 50, and a blood flow volume C of a nose C of the person 50 as the blood flow volumes of the at least two body parts. An emotion estimation unit 24A estimates the level of excitement of the person 50 as the emotion of the person 50 on the basis of the measured blood flow volume C of the nose C.

First, the physical condition estimation unit 22 estimates the level of stiffness in the shoulders of the person 50 as the physical condition of the person 50 on the basis of the blood flow volume A of the forehead A and the blood flow volume B of the neck B. The physical condition estimation unit 22 then corrects the estimated level of stiffness in the shoulders of the person 50 on the basis of the level of excitement of the person 50 estimated by the emotion estimation unit 24A.

An output control unit 13A then displays, as the output control according to the estimated physical condition of the person 50, the corrected level of stiffness in the shoulders on a screen 62 of the mobile terminal 60 owned by the person 50, such as a smartphone.

Although an estimated physical condition of a person is corrected on the basis of the person's emotion in the present embodiment and example, the operation performed is not limited to this. An estimated emotion of a person may be corrected on the basis of an estimated physical condition of the person, instead. This case will be described hereinafter as first and second modifications.

First Modification

A case will be described hereinafter, as the first modification, in which a physical condition to be estimated is hours of sleep of the day and an emotion to be estimated is a level of sleepiness.

Figure 18:
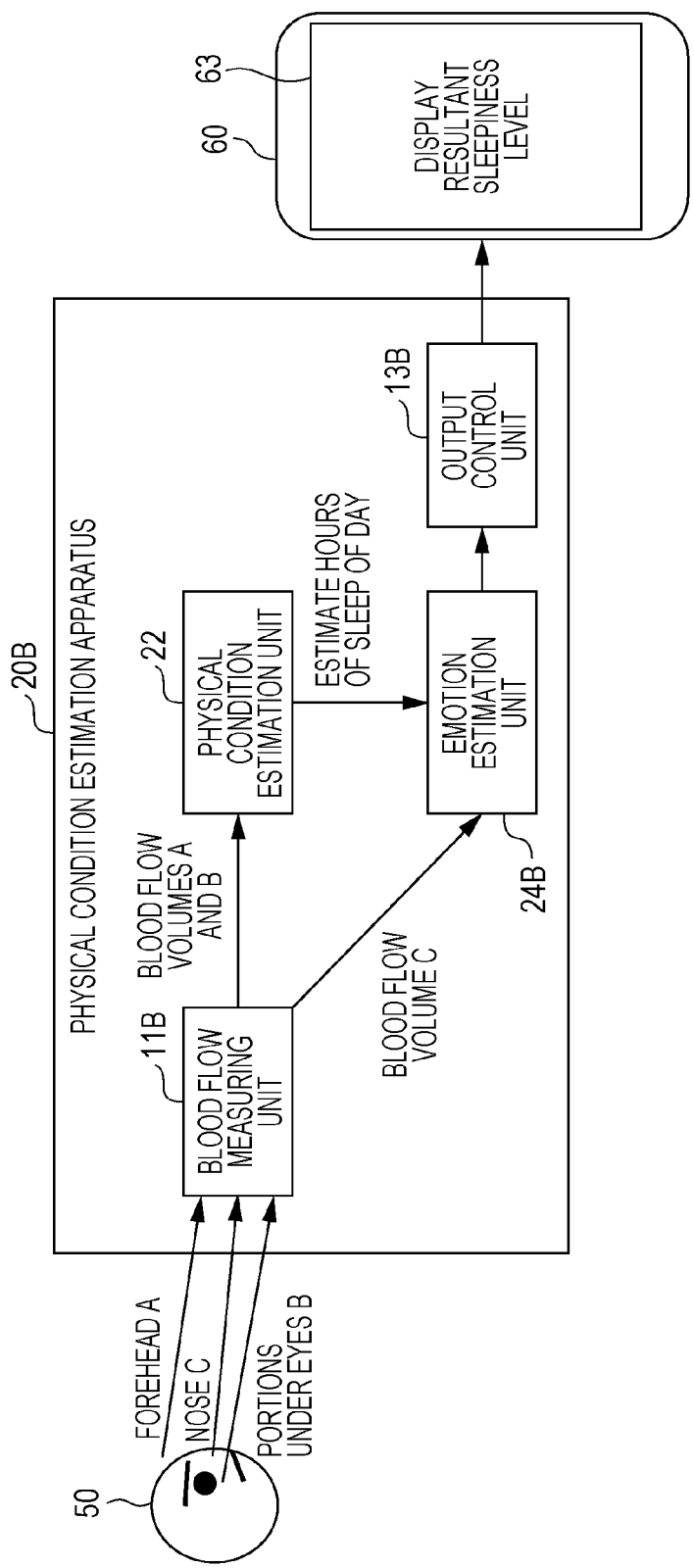
FIG. 18 is a diagram illustrating an example of output control performed by a physical condition estimation apparatus according to a first modification of the second embodiment.

FIG. 18 is a diagram illustrating an example of output control performed by a physical condition estimation apparatus 20B according to the first modification of the second embodiment.

In the present modification, for example, a blood flow measuring unit 11B measures the blood flow volume A of the forehead A of the person 50, the blood flow volume B of portions B under the eyes of the person 50, and the blood flow volume C of a nose C of the person 50 as the blood flow volumes of the at least two body parts. First, the physical condition estimation unit 22 estimates the hours of sleep of the day of the person 50 as the physical condition of the person 50 on the basis of the blood flow volume A of the forehead A and the blood flow volume B of the portions B under the eyes.

An emotion estimation unit 24B estimates the level of sleepiness of the person 50 as the emotion of the person 50 on the basis of the hours of sleep of the day of the person 50 estimated by the physical condition estimation unit 22 and the blood flow volume C of the nose C measured by the blood flow measuring unit 11B. More specifically, first, since the skin temperature of a person' nose increases when the person is sleepy, the emotion estimation unit 24B can estimates the level of sleepiness (arousal level) on the basis of the blood flow volume C measured by the blood flow measuring unit 11B. Next, the emotion estimation unit 24B may correct the level of sleepiness estimated on the basis of the blood flow volume C to a higher level of sleepiness if the hours of sleep of the day of the person 50 estimated by the physical condition estimation unit 22 is short (e.g., shorter than average hours of sleep of the person 50).

An output control unit 13B may, as output control, display the resultant level of sleepiness on a screen 63 of the mobile terminal 60, such as a smartphone, of the person 50.

The physical condition estimation apparatus 20B may thus correct an estimated emotion on the basis of an estimated physical condition.

The physical condition to be estimated may be the sense of warmth and coldness instead of the hours of sleep of the day. If estimating, as the physical condition of the person 50, that the person 50 is feeling cold, for example, the physical condition estimation apparatus 20B may reduce the level of sleepiness estimated as the emotion of the person 50. The physical condition to be estimated may be whether the shoulders of the person 50 are stiff, and the emotion to be estimated may be the comfort of the person 50. If estimating, as the physical condition of the person 50, that the shoulders of the person 50 are stiff, for example, the physical condition estimation apparatus 20B may reduce the comfort of the person 50 estimated as the emotion of the person 50.

Second Modification

Although a case in which the emotion of the person 50 is estimated from the blood flow volume of the nose of the person 50 has been described in the first modification, the emotion of the person 50 need not be estimated on the basis of the blood flow volume of the nose of the person 50. As described above, the emotion of the person 50 may be estimated on the basis of an image of the face of the person 50 captured by the camera section 241, instead. This case will be described hereinafter as the second modification. In the present modification, the physical condition to be estimated is the sense of warmth and coldness, and the emotion to be estimated is the level of sleepiness.

Figure 19:
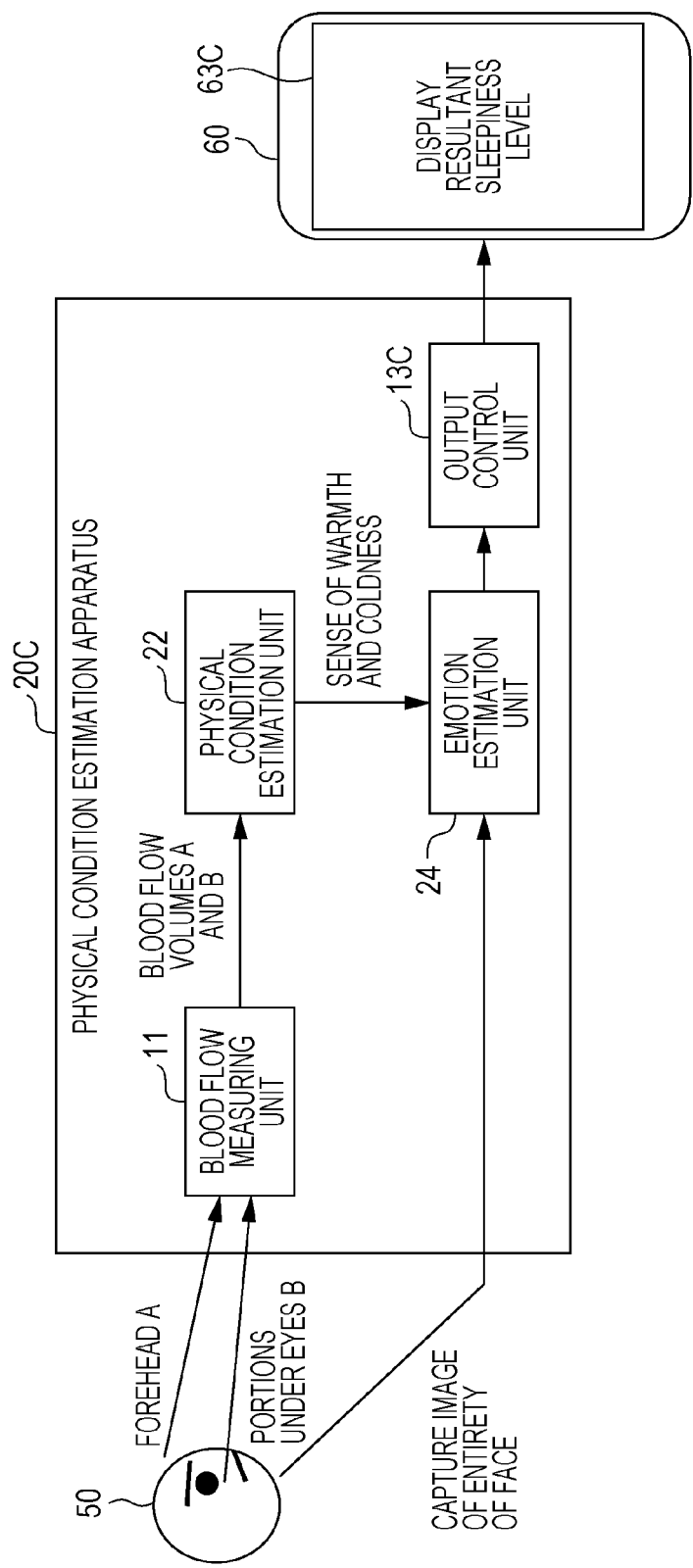
FIG. 19 is a diagram illustrating an example of output control performed by a physical condition estimation apparatus according to a second modification of the second embodiment.

FIG. 19 is a diagram illustrating an example of output control performed by a physical condition estimation apparatus 20C according to the second modification of the second embodiment.

In the present modification, for example, the blood flow measuring unit 11 measures the blood flow volume A of the forehead A of the person 50 and the blood flow volume B of the portions B under the eyes of the person 50 as the blood flow volumes of the at least two body parts. First, the physical condition estimation unit 22 estimates the sense of warmth and coldness of the person 50 as the physical condition of the person 50 on the basis of the blood flow volume A of the forehead A and the blood flow volume B of the portions B under the eyes.

The emotion estimation unit 24 estimates the level of sleepiness of the person 50 as the emotion of the person 50 on the basis of the sense of warmth and coldness of the person 50 estimated by the physical condition estimation unit 22 and an image of the entirety of the face of the person 50 captured by the emotion estimation unit 24.

More specifically, first, the emotion estimation unit 24 captures an image of the entirety of the face of the person 50. The emotion estimation unit 24 then estimates a heartrate of the person 50 from slight variation in the complexion of the person 50 and determines a position along the arousal axis illustrated in FIG. 14. The emotion estimation unit 24 also determines a position along the pleasure axis from a facial expression estimated from the image of the entirety of the face of the person 50. As a result, the emotion estimation unit 24 can estimates the level of sleepiness of the person 50 as the emotion of the person 50 from the captured image of the entirety of the face of the person 50. The emotion estimation unit 24 then corrects the level of sleepiness estimated from the image of the entirety of the face of the person 50 on the basis of the sense of warmth and coldness of the person 50 estimated by the physical condition estimation unit 22. If the physical condition estimation unit 22 estimates, as the physical condition of the person 50, that the person 50 is feeling cold, for example, the emotion estimation unit 24 may reduce the level of sleepiness of the person 50 estimated as the emotion of the person 50.

An output control unit 13C may display, as output control, the resultant level of sleepiness on a screen 63C of the mobile terminal 60, such as a smartphone, of the person 50.

The physical condition estimation apparatus 20C may thus correct an estimated emotion on the basis of an estimated physical condition.

Although the processes in the present disclosure has been described with reference to the first and second embodiments, a person or an apparatus that performs each process is not particularly limited.

As described above, the physical condition estimation apparatus may include the blood flow measuring unit, the physical condition estimation unit, and the output control unit, for example, but may include only the physical condition estimation unit or only the physical condition estimation unit and the output control unit. Alternatively, The physical condition estimation unit and the output control unit may be achieved by a cloud server provided in a place different from a place where the local apparatus is provided. In this case, the cloud server and the local apparatus may share processing or control. For example, the cloud server may perform heavy processing or control, and the local apparatus may perform light processing or control. The cloud server and the local apparatus may together be referred to as a "physical condition estimation apparatus".

The physical condition estimation apparatus may be implemented as a processor or the like incorporated into a particular locally provided apparatus (described hereinafter).

(1) More specifically, the physical condition estimation apparatus is a computer system including a microprocessor, a read-only memory (ROM), a random-access memory (RAM), a hard disk unit, a display unit, a keyboard, and a mouse. The RAM or the hard disk unit stores a computer program. When the microprocessor operates in accordance with the computer program, the physical condition estimation apparatus achieves functions thereof. The computer program includes a plurality of command codes for issuing instructions to the computer system in order to achieve certain functions.

(2) Part or all of the components of the physical condition estimation apparatus may be implemented as a single large-scale integration (LSI) circuit. A system LSI circuit is a super-multifunctional LSI circuit fabricated by integrating a plurality of components on a single chip. More specifically, the system LSI circuit is a computer system including a microprocessor, a ROM, and a RAM. The RAM stores a computer program. When the microprocessor operates in accordance with the computer program, the system LSI circuit achieves functions thereof.

(3) Part or all of the components of the physical condition estimation apparatus may be implemented as an integrated circuit (IC) or a separate module removably attached to the physical condition estimation apparatus. The IC card or the module is a computer system including a microprocessor, a ROM, and a RAM. The IC card or the module may also include the super-multifunctional LSI circuit. When the microprocessor operates in accordance with a computer program, the IC card or the module achieves functions thereof. The IC card or the module may be tamper-resistant.

(4) The present disclosure may be the above-described method. The present disclosure may be a computer program that implements the method using a computer or may be a digital signal including the computer program.

(5) The present disclosure may be a computer-readable recording medium storing the computer program or the digital signal, such as a flexible disk, a hard disk, a CD-ROM, a magneto-optical (MO) disk, a digital versatile disc (DVD), a DVD-ROM, a DVD-RAM, a Blu-ray disc (BD; registered trademark), or a semiconductor memory. The present disclosure may be the digital signal stored in one of these computer-readable recording media.

The present disclosure may be the computer program or the digital signal transmitted through an electrical communication line, a wireless or wired communication line, a network typified by the Internet, datacasting, or the like.

The present disclosure may be a computer system including a microprocessor and a memory. The memory may store the computer program, and the microprocessor may operate in accordance with the computer program.

The present disclosure may be implemented as an independent computer system by recording the computer program or the digital signal on one of the computer-readable recording media and transporting the computer-readable recording medium or by transporting the computer program or the digital signal through the network or the like.

(6) The above embodiments and modifications may be combined with one another.

(7) A person's physical condition may be different from those described in the first and second embodiments. A person's physical condition may be an epileptic seizure, Meniere's syndrome, dizziness, or the like. In this case, a physiological value such as the blood flow volume of a person may or may not be used in order to estimate the person's physical condition. A method for estimating a person's physical condition other than those described in the first and second embodiments and the like will be described hereinafter.

Epileptic Seizure

A method for estimating an epileptic seizure as a person's physical condition and an output at a time when an epileptic seizure has been estimated will be described.

The occurrence of an epileptic seizure can be estimated (detected) from a person's line of sight or respiration or the diameter of the person's pupils. This is because it is known that a person's line of sight is fixed, the person's respiration becomes irregular, and light reflex from the person's pupils disappears due to an epileptic seizure. An epileptic seizure, therefore, can be estimated (detected) as a person's physical condition by measuring the person's light of sight or respiration or the diameter of the person's pupils.

Figure 20:
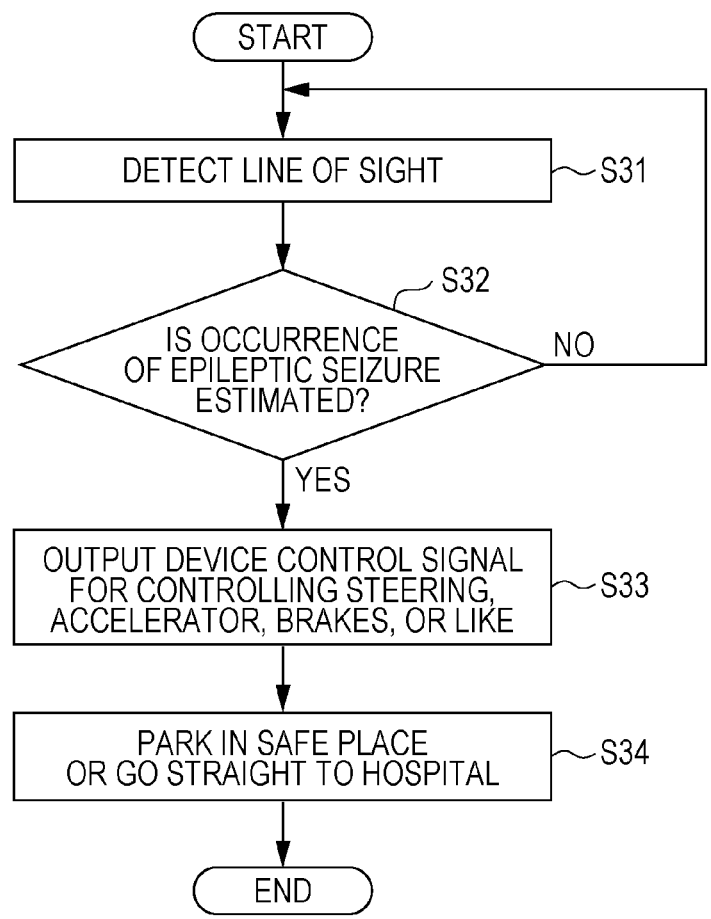
FIG. 20 is a flowchart illustrating an example of estimation of an epileptic seizure and an output control method.

FIG. 20 is a flowchart illustrating an example of the estimation of an epileptic seizure and an output control method.

As illustrated in FIG. 20, first, for example, a person's line of sight is detected (S31), and whether an epileptic seizure has occurred to the person is estimated on the basis of the person's line of sight (S32). Whether an epileptic seizure has occurred to the person may be estimated using one, some, or all of the person's line of sight and respiration and the diameter of the person's pupils.

Next, if it is estimated that an epileptic seizure has not occurred to the person (NO in S32), the process returns to S31. On the other hand, if it is estimated that an epileptic seizure has occurred to the person (YES in S32) and the person is inside a vehicle, a device control signal for controlling a device such as brakes, an accelerator, or an active suspension of the vehicle is output (S33).

Furthermore, if the person is inside an automobile in an automated driving mode, the automobile automatically parks in a safe place or goes to a closest hospital (S34). In S34, the automobile may call a closest ambulance or security center.

Meniere's Syndrome and Dizziness

Next, a method for estimating Meniere's syndrome or dizziness as a person's physical condition and an output at a time when Meniere's syndrome or dizziness has been estimated will be described.

By detecting a person's line of sight, whether Meniere's syndrome or dizziness has occurred to the person can be estimated (detected). This is because it is known that a person's line of sight runs in circles when dizziness or Meniere's syndrome has occurred to the person.

If it is estimated (detected) that Meniere's syndrome or dizziness has occurred to a person and the person is inside an automobile in an automated driving mode, a device such as brakes, an accelerator, or an active suspension of the vehicle may be controlled in such a way as to automatically park the automobile in a safe place. Needless to say, the automobile may immediately call a closest ambulance or security center or may go to a closest hospital through automated driving.

Various Diseases

Alternatively, one of the following diseases may be estimated (detected) as a person's physical condition from a constituent or a secretion of exhaled air.

If the amount of ammonia included in a person's exhaled air is large, for example, a decrease in a kidney or liver function of the person, deterioration of an intestinal environment, or gout can be detected. If the amount of nitric oxide included in a person's exhaled air is large, for example, bronchial asthma or sleepiness of the person can be detected. If the amount of hydrogen sulfide included in a person's exhaled air is large, for example, a gastrointestinal disorder of the person can be detected. If the amount of 3-methyl-3-sulfanyl-hexan-1-ol included in a person's exhaled air is large, for example, it can be estimated that the person is psychologically stressed.

For example, a sensor capable of detecting one of the above-mentioned chemical substances may be provided on a desk or a mouse in a person's office, and if one of the above-mentioned disorders is detected as the person's physical condition, the person or a medical department may be notified of the detection. As a result, the person can be protected from various diseases.

Deep Body Temperature

The deep body temperature of a person may be estimated as the person's physical condition.

By detecting the body surface temperature of a person, the deep body temperature of the person can be estimated. The temperature of the forehead, for example, is known to be close to the deep body temperature. By detecting the temperature of the forehead or the like using a thermal camera, the deep body temperature can be estimated. If ambient temperature is also measured and the body surface temperature is corrected, the deep body temperature can be estimated more accurately. The deep body temperature may be estimated more accurately by also measuring the temperature of a body part such as an eyeball.

An example of output control when the deep body temperature is estimated (detected) will be described hereinafter.

Figure 21:
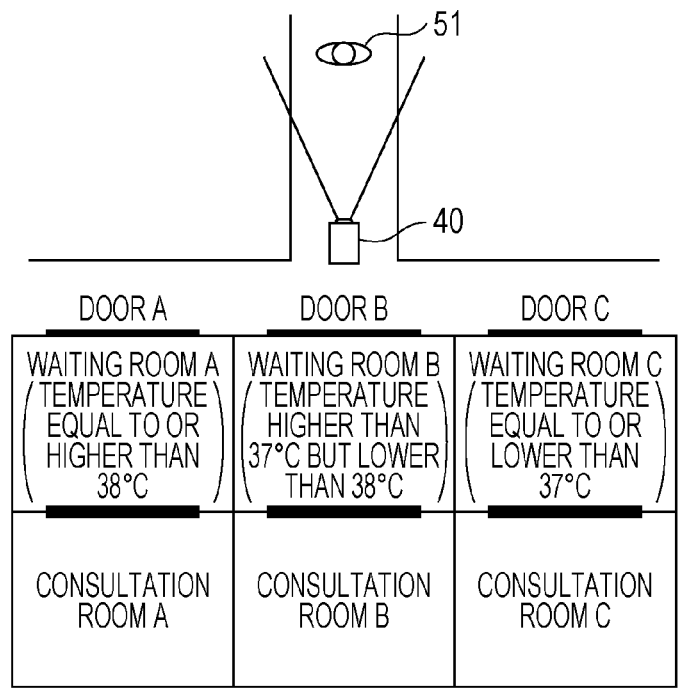
FIG. 21 is a diagram illustrating an example of output control depending on a result of detection of deep body temperature.
Figure 22:
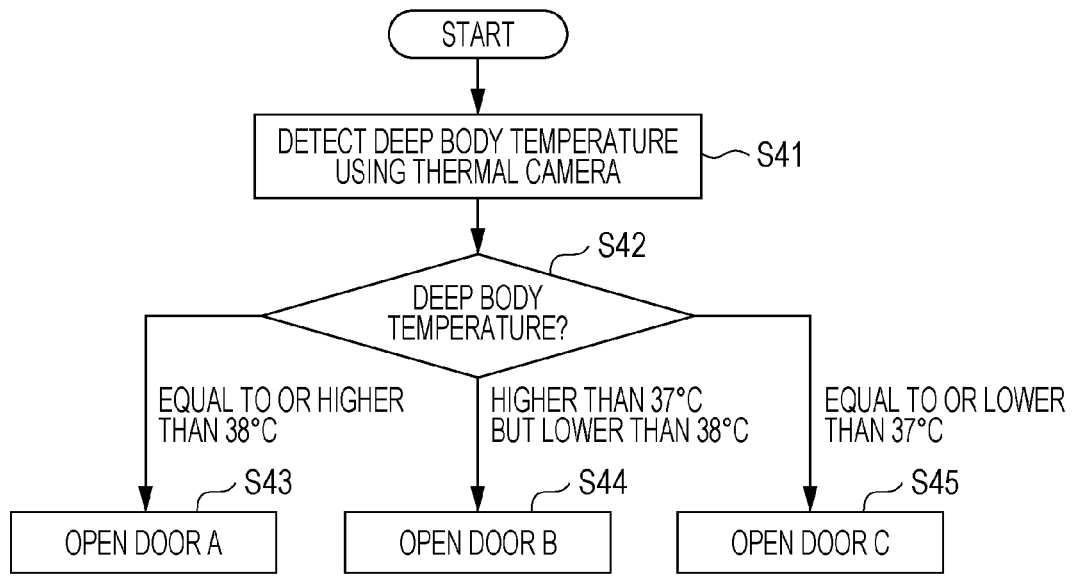
FIG. 22 is a flowchart illustrating an example of an output control method depending on the result of the detection of the deep body temperature.

FIG. 21 is a diagram illustrating an example of output control depending on a result of detection of deep body temperature. FIG. 22 is a flowchart illustrating an example of an output control method depending on the result of the detection of the deep body temperature.

As illustrated in FIG. 21, the deep body temperature of a patient 51 in front of a hospital can be measured in a noncontact manner by detecting the temperature of the forehead of the patient 51 using a thermal camera 40. Since a heat generation state of the patient 51 can be detected by detecting the deep body temperature of the patient 51 before the patient 51 enters a hospital, for example, one of entrances to the hospital (waiting rooms) may automatically open in accordance with the heat generation state.

That is as illustrated in FIG. 22, first, the deep body temperature of the patient 51 is detected using the thermal camera 40 (S41), and it is determined whether the deep body temperature of the patient 51 is equal to or higher than 38° C., higher than 37° C. but lower than 38° C., or equal to or lower than 37° C. (S42).

In S42, if the deep body temperature of the patient 51 is equal to or higher than 38° C., for example, a door A of a waiting room A automatically opens (S43). If the deep body temperature of the patient 51 is higher than 37° C. but lower than 38° C., a door B of a waiting room B automatically opens (S44). If the deep body temperature of the patient 51 is equal to or lower than 37° C., a door C of a waiting room C automatically opens (S45).

As a result, a patient 51 having a high fever enters a room different from one in which a patient 51 whose temperature is normal is waiting, and the patient 51 whose temperature is normal does not get infected from the patient 51 having a high fever.

The thresholds of deep body temperature may be different from those illustrated in FIGS. 21 and 22, and may be adjusted in accordance with age. This is because it is known that temperatures of younger people are relatively high. A patient's age may be registered to the patient's medical card, and the patient may hold the medical card out toward a reader. The reader and the thermal camera 40 together achieve the estimation of the deep body temperature of the patient.

A taxi may implement this estimation method. In this case, a driver of the taxi can, as necessary, decline to pick up a patient having a high fever, and a secondary infection to the driver can be prevented. In addition, in a public transportation system such as a train, different cars may be provided for people whose temperatures are high and people whose temperatures are low. In this case, the prevalence of a disease can be suppressed in the public transportation system.

The method for estimating deep body temperature and the output control are not limited to these examples.

For example, the deep body temperature at a time of rising may be measured (estimated) daily. In this case, a woman's menstrual period can be estimated. When the woman's skin tends to be dry during the estimated menstrual period, a humidifier or an air conditioner may be automatically adjusted to prevent the woman's skin from becoming dry. When the woman tends to get irritated, an audio system may automatically select relaxing songs.

The timing at which the deep body temperature is measured daily is not limited to the time of rising. The deep body temperature may be measured at any timing insofar as the measurement can be performed under the same condition. For example, the deep body temperature may be measured at a washstand in the morning.

For example, the deep body temperature may be measured when a person arrives at his/her office. By measuring the deep body temperature when the person holds a card out toward a reader at an entrance of the office, for example, the person and the deep body temperature can be associated with each other, and a worker having a fever can be identified. A boss who has been informed that the worker has a fever can adjust a work schedule or urge the worker to go home, in order to maintain the worker's health and prevent infection to other workers.

Dryness of Skin

A dryness level of a person's skin may be estimated as the person's physical condition.

This is because the dryness level of a person's skin can be estimated by measuring a water content level of the person's skin. If the dryness level is equal to or lower than a certain value, that is, if the water content level of the person's skin is equal to or lower than a certain value, a humidifier in a room where the person stays may be operated to humidify the room for esthetic purposes.

Metabolic Rate

A person's metabolic rate may be estimated as the person's physical condition.

By measuring the temperature of a person's collarbone using a thermal camera, a radiation thermometer, or the like, the person's metabolic rate can be estimated. It is known that when there is brown fat, the metabolic rate increases. The brown fat is located around the collarbone and generates heat. By measuring the temperature of the person's collarbone, therefore, the person's metabolic rate can be estimated.

If a calorie intake of a person is larger than an estimated metabolic rate, for example, a warning may be issued to the person. In this case, the person can be prevented from getting overweight.

Others

How a person is seated on a chair may be estimated (detected) as the person's physical condition.

By providing a sensor for measuring the distribution of pressure in a seat of a chair, how a person is seated on the chair can be detected. A body part likely to ache may be estimated from the detected information and heated to prevent the pain.

Alternatively, shortness of breath of a person may be estimated (detected) as the person's physical condition.

Shortness of breath a person can be detected from a respiratory rate or the oxygen saturation of the person. If shortness of breath is detected, the person may be notified the rhythm of respiration as a sound or the like. As a result, the rhythm of the respiration of the person can be adjusted. By notifying the person of a rhythm of respiration slightly slower than the actual rhythm of respiration of the person and gradually slowing down the rhythm of respiration, the respiration of the person can be adjusted.

Alternatively, palpitations of a person due to tension or the like may be estimated (detected) as the person's physical condition by measuring the person's heartrate.

If palpitations of a person due to tension or the like are detected, a sound whose rhythm is slightly slower than the actual heartrate may be output to the person. As a result, the person's heartrate can be decreased to relax the person. If the person is going to play a match and needs to be tense, a sound whose rhythm is slightly faster than that of an actual heartrate when the person is at rest may be output to the person. As a result, an ideal tension may be achieved.

An insurance fee of life insurance or medical insurance may be adjusted in accordance with a detected type of physical condition, a degree of the physical condition, and a time at which the physical condition has been detected. As a result, an insurance fee for a health person can be decreased, and an insurance fee for a sick person can be increased, which is fair to all insured persons.

If a sick person is detected in a movie theater or the like, a clerk may be notified of the detection. For example, the clerk may help the person leave the movie theater or the like. As a result, it becomes possible to prevent the sick person from interrupting screening.

Although the methods for estimating a person's physical condition other than those according to the first and second embodiments have been described, the methods used are not limited to these examples. A person's emotion may be estimated using methods other than that according to the second embodiment. Such methods will be described hereinafter while taking examples.

Level of Irritation

A level of irritation of a person, for example, may be estimated (detected) as the person's emotion.

The level of irritation can be estimated from a person's facial expression or blood flow volume. This is because it is known that a person's facial expression reflects irritation. This is also because it is known that when a person is irritated, a sympathetic nervous system becomes active and peripheral blood flow decreases. Here, the level of irritation of a person may be estimated from both the person's facial expression and blood flow volume or either the person's facial expression or the person's blood flow volume.

If the level of irritation of a person is estimated and the person is driving, the sound of an engine of the person's automobile may be output inside the automobile to make the person feel that the automobile is running faster than an actual speed. As a result, it becomes possible to prevent the person from driving too fast. Needless to say, if irritation of the person is estimated, the sensitivity of an accelerator of the automobile may be reduced to prevent a sudden start or the sensitivity of brakes of the automobile may be reduced to prevent a sudden stop, instead.

Level of Sleepiness

A level of sleepiness of a person, for example, may be estimated (detected) as the person's emotion.

This is because it is known that a person's facial expression reflects sleepiness. This is also because it is known that when a person is sleepy, a parasympathetic nervous system becomes active and a heartrate becomes irregular, peripheral blood flow increases and the temperature of the peripheral skin increases, and blood pressure decreases due to expansion of blood vessels. It is also known that when a respiratory rate decreases, oxygen concentration decreases, and a person becomes sleepy.

The level of sleepiness of a person may thus be estimated from the person's facial expression, heartrate, respiration, blood pressure, blood flow volume, or skin temperature.

Here, the level of sleepiness of a person may be estimated from one, some, or all of the person's facial expression, heartrate, respiration, blood pressure, blood flow volume, and skin temperature.

Alternatively, a combination of these pieces of information with which estimation accuracy becomes highest may be learned, and a different combination may be used for each person.

This is because some persons' facial expression clearly reflects sleepiness whereas other person's facial expression hardly reflects sleepiness. When a person's facial expression clearly reflects sleepiness, the person's facial expression may be used to estimate the level of sleepiness. By detecting the level of sleepiness while combination the person's facial expression with another physiological value, needless to say, the level of sleepiness can be accurately estimated. A combination used may be changed for each level of sleepiness to be detected. In addition, some persons' blood pressure significantly decreases when the persons begin to become sleepy, whereas other persons' blood pressure does not. When a person falls into the former case, blood pressure may be used to estimate the level of sleepiness at an early timing.

These are examples, and another physiological index may be used to estimate the level of sleepiness as necessary. In this case, the level of sleepiness can be accurately estimated. The same holds when a high level of sleepiness is estimated. Any physiological index may be used. As a result, an optimal physiological index can be learned and used in accordance with the level of sleepiness to be detected, thereby achieving accurate estimation of the level of sleepiness.

If it is detected (estimated) that a person is sleepy and the person is driving, the vehicle may be ventilated to increase oxygen concentration inside the vehicle. In doing so, the level of sleepiness of the person can be reduced. Alternatively, the person's sense of speed may be increased and an arousal level of the person may be increased by opening a partition between an engine room and the driver's seat to let the sound of an engine be heard by the person. Furthermore, the arousal level of the person may be increased by changing the rigidity of a suspension of the vehicle and transmitting vibration to the person.

Method for Detecting Each Physiological Value

A method for detecting each physiological value will be described hereinafter.

Heartrate

The heartrate can be detected by detecting slight variation in the skin color of a face whose image has been captured by a camera. This is because especially a green component of the skin color of the face varies depending on the heartrate.

Alternatively, the heartrate may be detected by detecting variation in the temperature of a temperature range corresponding to the skin of the face whose image has been captured by a thermal camera. This is because the temperature of the face whose image has been captured by the thermal camera varies depending on the heartrate and the heartrate can be detected by detecting variation in the temperature of the temperature range corresponding to the skin.

Alternatively, infrared light may be radiated onto an ear robe, a finger, or the like and the heartrate may be detected from variation in reflected infrared light. Alternatively, vibration caused by heartbeats may be detected using a sheet sensor or the like, and the heartrate may be detected from a waveform of the heartbeats. Any other method may be used.

Blood Pressure

The blood pressure can be obtained from a pulse wave propagation time. The pulse wave propagation time is a time taken for blood in the heart to reach a certain peripheral part.

When blood pressure drops, the pulse wave propagation time increases, and when blood pressure rises, the pulse wave propagation time decreases. The pulse wave propagation time can be obtained from a difference between a time of a peak of a pulse wave obtained from an image of the face captured by a camera and a time of a peak of the pulse wave obtained from an image of a body part other than the face (the neck, a hand, or the like). The pulse wave propagation time may be obtained from a difference between times of peaks of a pulse wave at two facial parts (e.g., the jaw and the forehead), instead of the face and a body part other than the face.

Alternatively, the vibration of the heart may be obtained from a milliwave sensor or the like, and a pulse wave in the face may be detected from slight variation in the color of an image of the face captured by a camera. The pulse wave propagation time may then obtained from a difference between a peak of the vibration of the heart and a peak of the pulse wave in the face, and the blood pressure may be obtained by estimating variation in the blood pressure.

Skin Moisture Level

A skin moisture level can be measured by radiating near-infrared light having an absorption wavelength of water (960 nm) onto the skin and detecting the amount of returning light. This is because when the skin moisture level is high, the radiated near-infrared light is absorbed and the amount of returning light decreases.

A water content level (skin moisture level) may be estimated from the hardness of the skin by radiating ultrasonic waves or air and detecting variation at the time using a milliwave sensor or the like. This is because it is known that the skin hardens when the skin moisture level decreases.

Blood Sugar Level

A blood sugar level can be obtained by radiating infrared light onto an eyeball and detecting the amount of returning light. This is because the spectrum of a part of the eyeball (aqueous humor) includes an absorption wavelength of sugar (around 1,650 nm), and the amount of returning light decreases when the blood sugar level is high.

The blood sugar level may be estimated from optical rotation of the part of the eyeball (aqueous humor). This is because the optical rotation increases as the blood sugar level becomes higher. Any other method may be used to estimate the blood sugar level.

Constituent of Exhaled Air

A constituent of exhaled air can be detected on the basis of the amount of absorption at an absorption wavelength of the constituent to be detected (e.g., around 225 nm in the case of nitric oxide).

A constituent of exhaled air can be detected by radiating light having an absorption wavelength of the constituent and detecting the amount of light that has passed through the exhaled air. A spectrum may be detected, needless to say, using chromatography. Any other method may be used.

Respiration

Respiration can be detected by, in a camera image, radiating infrared light having a rectangular pattern onto a subject and detecting a wavelength of the respiration from variation in the pattern.

The respiration may be detected using visible light instead of infrared light, and the pattern to be radiated need not be a rectangular pattern. A milliwave may be radiated, and the respiration may be detected from a Doppler shift in a reflected wave, instead. Alternatively, the respiration may be detected using a time-of-flight (TOF) sensor.

It is known that the temperature of the portion under the nostrils decreases during inhalation and increases during exhalation. A waveform of respiration, therefore, may be detected from variation in the temperature of the portion under the nostrils using a thermal image.

The present disclosure can be applied to a method for estimating a physical condition, a physical condition estimation apparatus, and a program that estimate a person's physical condition. The present disclosure can be applied especially to a method for estimating a physical condition, a physical condition estimation apparatus, and a recording medium storing a program that is incorporated into devices in vehicles, offices, and living spaces and device applications that control such devices.

What is claimed is:

1. A method for estimating a person's physical condition, the method comprising:

simultaneously measuring, with a sensor, blood flow volumes of at least two body parts of the person, wherein at least two body parts of the person includes a first body part being the person's forehead and a second body part being different from the person's forehead; and estimating, with a processor, the person's physical condition on a basis of a difference between a first blood flow volume of the first body part being the person's forehead and a second blood flow volume of the second body part being different from the person's forehead, which are simultaneously measured with the sensor, wherein, in a case where the second body part is a facial portion under the person's eye, above the person's lower portion of nose and excluding the person's nose and ears, the physical condition is at least one of hours of sleep of the person, a sense of warmth and coldness of the person, a level of urgency at which the person wants to go to a toilet, a level of carsickness of the person, a risk of heat shock of the person, a person's risk of a vascular disorder caused by an increase in blood pressure during defecation, a level of intoxication of the person, the person's driving skills, the person's hunger level, the person's fatigue level, or the person's depression levels, in a case where the second body part is one of the person's nose, the person's lips, person's hand and the person's feet, the physical condition is a sense of warmth and coldness of the person, and in a case where the second body part is the person's neck, the physical condition is a sense of whether the person's shoulders are stiff.

2. The method according to claim 1,
wherein, the blood flow volume of the second body part varies depending on the person's physical condition.

3. The method according to claim 1, further comprising:
estimating the person's emotion on a basis of a physiological value of the person; and correcting the person's physical condition estimated in the estimating the person's physical condition on the basis of the person's emotion estimated in the estimating the person's emotion.

4. The method according to claim 3,
wherein the physiological value of the person is one of the blood flow volumes of the at least two body parts.

5. The method according to claim 3,
wherein the physiological value of the person is a blood flow volume of a body part different from the at least two body parts.

6. The method according to claim 3,
wherein the physiological value of the person is at least one of complexion, a heartrate, variation in the heartrate, a ratio of a low-frequency component to a high frequency component of the variation in the heartrate, R-R intervals, a pulse wave, variation in the pulse wave, a brain wave, a respiratory rate, respiratory volume, blood flow, variation in the blood flow, blood pressure, variation in the blood pressure, oxygen saturation, movement of a body part, movement of a body muscle, movement of a facial muscle, body temperature, skin temperature, skin conductance, skin resistance, the amount of sweat, and a sweating rate.

7. The method according to claim 1,
wherein, in the simultaneously measuring, the blood flow volumes of the at least two body parts are measured in a noncontact manner by radiating light having a certain wavelength onto the at least two body parts and receiving light having wavelengths different from each other.

8. The method according to claim 7,
wherein, in the simultaneously measuring, the blood flow volumes of the at least two body parts are measured using a camera as the sensor.

9. A physical condition estimation apparatus comprising:
a sensor adapted to simultaneously measure blood flow volumes of at least two body parts of a person, wherein at least two body parts of the person includes a first body part being the person's forehead and a second body part being different from the person's forehead; and
a processor that estimates the person's physical condition on a basis of a difference between a first blood flow volume of the first body part being the person's forehead and a second blood flow volume of the second body part being different from the person's forehead simultaneously measured with the sensor, wherein,
in a case where the second body part is a facial portion under the person's eye, above the person's lower portion of nose and excluding the person's nose and ears, the physical condition is least one of hours of sleep of the person, a sense of warmth and coldness of the person, a level of urgency at which the person wants to go to a toilet, a level of carsickness of the person, a risk of heat shock of the person, a person's risk of a vascular disorder caused by an increase in blood pressure during defecation, a level of intoxication of the person, the person's driving skills, the person's hunger level, the person's fatigue level, or the person's depression levels, in a case where the second body part is one of the person's nose, the person's lips, person's hand and the person's feet, the physical condition is a sense of warmth and coldness of the person, and in a case where the second body part is the person's neck, the physical condition is a sense of whether the person's shoulders are stiff.

10. A non-transitory computer-readable recording medium storing a program for estimating a person's physical condition, the program causing a computer to:
cause a sensor of the computer to simultaneously measure blood flow volumes of at least two body parts of the person, wherein at least two body parts of the person includes a first body part being the person's forehead and a second body part being different from the person's forehead; and
estimate the person's physical condition on a basis of a relationship between a first blood flow volume of the first body part being the person's forehead and a second blood flow volume of the second body part being different from the person's forehead, which are simultaneously measured with the sensor, wherein,
in a case where the second body part is a facial portion under the person's eye, above the person's lower portion of nose and excluding the person's nose and ears, the physical condition is least one of hours of sleep of the person, a sense of warmth and coldness of the person, a level of urgency at which the person wants to go to a toilet, a level of carsickness of the person, a risk of heat shock of the person, a person's risk of a vascular disorder caused by an increase in blood pressure during defecation, a level of intoxication of the person, the person's driving skills, the person's hunger level, the person's fatigue level, or the person's depression levels in a case where the second body part is one of the person's nose, the person's lips, person's hand and the person's feet, the physical condition is a sense of warmth and coldness of the person, and in a case where the second body part is the person's neck, the physical condition is a sense of whether the person's shoulders are stiff.

* * * * *